United States Patent
Nitta et al.

(10) Patent No.: US 12,100,927 B2
(45) Date of Patent: Sep. 24, 2024

(54) LIGHT-EMITTING DEVICE, AND ELECTRONIC DEVICE AND INSPECTION METHOD USING SAME

(71) Applicant: Panasonic Intellectual Property Management Co., Ltd., Osaka (JP)

(72) Inventors: Mitsuru Nitta, Kyoto (JP); Takeshi Abe, Osaka (JP); Shozo Oshio, Osaka (JP)

(73) Assignee: Panasonic Intellectual Property Management Co., Ltd., Osaka (JP)

( * ) Notice: Subject to any disclaimer, the term of this patent is extended or adjusted under 35 U.S.C. 154(b) by 457 days.

(21) Appl. No.: 17/613,792

(22) PCT Filed: Apr. 21, 2020

(86) PCT No.: PCT/JP2020/017164
§ 371 (c)(1),
(2) Date: Nov. 23, 2021

(87) PCT Pub. No.: WO2020/241119
PCT Pub. Date: Dec. 3, 2020

(65) Prior Publication Data
US 2022/0239057 A1    Jul. 28, 2022

(30) Foreign Application Priority Data
May 27, 2019    (JP) .................... 2019-098537

(51) Int. Cl.
*H01S 5/00*    (2006.01)
*A61B 1/06*    (2006.01)
*G02B 23/24*   (2006.01)

(52) U.S. Cl.
CPC .......... *H01S 5/0087* (2021.01); *A61B 1/0653* (2013.01); *G02B 23/2469* (2013.01)

(58) Field of Classification Search
CPC .. H01S 5/0087; A61B 1/0653; G02B 23/2469
See application file for complete search history.

(56) References Cited

U.S. PATENT DOCUMENTS

| 5,422,907 A * | 6/1995 | Bhargava ................. H01S 3/06 372/74 |
| 5,446,286 A * | 8/1995 | Bhargava ................. G01T 1/20 257/17 |

(Continued)

FOREIGN PATENT DOCUMENTS

| EP | 3777647 A1 | 2/2021 |
| EP | 3961827 A1 | 2/2022 |

(Continued)

OTHER PUBLICATIONS

International Search Report for corresponding Application No. PCT/JP2020/017164, mailed Jul. 14, 2020.

(Continued)

*Primary Examiner* — Hugh Maupin
(74) *Attorney, Agent, or Firm* — Renner, Otto, Boisselle & Sklar, LLP

(57) ABSTRACT

A light emitting device includes a light source that emits a primary light having a light energy density exceeding 0.5W/mm², and a first phosphor that absorbs the primary light to convert the primary light into a first wavelength-converted light having a wavelength longer than that of the primary light. The first phosphor includes a compound serving as a host, the compound being a simple oxide including one kind of metal element or a composite oxide including a plurality of different kinds of the simple oxide as an end member. When an energy conversion value at a peak wavelength of the primary light is E1 electron volts and an energy conversion value at a fluorescence peak wavelength of the first wavelength-converted light is E2 electron volts, a bandgap (Continued)

energy of a crystal of the simple oxide is larger than a sum of the E1 electron volts and the E2 electron volts.

18 Claims, 15 Drawing Sheets

(56) References Cited

U.S. PATENT DOCUMENTS

| | | | |
|---|---|---|---|
| 7,927,661 B2 | 4/2011 | Jones | |
| 8,684,562 B2* | 4/2014 | Ishimori | C04B 35/44 362/293 |
| 9,905,069 B1* | 2/2018 | Goltsos | G07D 7/2041 |
| 2004/0062699 A1* | 4/2004 | Oshio | C04B 35/01 252/301.4 F |
| 2008/0164466 A1* | 7/2008 | Rioux | C09K 9/02 438/38 |
| 2009/0237661 A1 | 9/2009 | Yamazoe | |
| 2011/0101387 A1* | 5/2011 | Kinomoto | C09K 11/65 257/89 |
| 2011/0126889 A1* | 6/2011 | Bourke, Jr. | H01L 31/055 362/552 |
| 2012/0113672 A1* | 5/2012 | Dubrow | B32B 5/16 977/774 |
| 2012/0132930 A1* | 5/2012 | Young | H05K 1/0313 257/E31.127 |
| 2014/0285997 A1* | 9/2014 | Nitta | F21K 9/64 252/301.4 F |
| 2015/0340559 A1* | 11/2015 | Asadi | H01L 33/28 252/519.1 |
| 2015/0357532 A1 | 12/2015 | Onuma | |
| 2016/0000018 A1 | 1/2016 | Van Elmpt | |
| 2018/0212112 A1 | 7/2018 | Nitta | |
| 2018/0348577 A1* | 12/2018 | Pousthomis | G02F 1/133514 |
| 2020/0010760 A1 | 1/2020 | Ueda | |

FOREIGN PATENT DOCUMENTS

| | | |
|---|---|---|
| EP | 3961828 A1 | 2/2022 |
| JP | 2009-231483 A | 10/2009 |
| JP | 4575362 B | 8/2010 |
| JP | 2016-504044 A | 2/2016 |
| WO | 2014/103671 A1 | 7/2014 |
| WO | 2018/008282 A1 | 1/2018 |
| WO | 2018/163830 A1 | 9/2018 |
| WO | 2019/063297 A1 | 4/2019 |
| WO | 2019/063309 A1 | 4/2019 |

OTHER PUBLICATIONS

Written Opinion for corresponding Application No. PCT/JP2020/017164, mailed Jul. 14, 2020.
O.B. Shchekin et al., "Excitation dependent quenching of luminescence in LED phosphors", Phys. Status Solidi, RRL 10, pp. 310-314 (2016) (cited in specification).
A. Lenef et al., Proc. SPIE 8841, Current Developments in Le s Design and Optical Engineering XIV, 884107 (2013) (cited in specification).
John Robertson, "Band offsets of wide-band-gap oxides and implications for future electronic devices", J. Vac. Sci. Technol., B 18.3., pp. 1785-1791 (2000) (cited in specification).
Masataka Higashiwaki et al., "Crystal Growth and Device Application of Gallium Oxide (Ga2O3)", Surface Science, vol. 35, No. 2, pp. 102-107, (2014) (cited in specification)(with English Abstract).
A. V. Emeline et al., "Photostimulated Generation of Defects and Surface Reactions on a Series of Wide Band Gap Metal-Oxide Solids", The Journal of Physical Chemistry, B 103, (43), (1999) pp. 9190-9199 (cited in specification).
Shuichi Matsunari, "First principles calculations for development of inorganic material", Tsubame Industrial Application Trial Use Results Report 2014 (Fiscal year Heisei 26) (cited in specification).
Keisuke Kobayashi, "Gate dielectric film evaluation by Soft X-ray Photoelectron Spectroscopy", SPring-8 Industrial Application Promotion Office (cited in specification).
V. V. Afanas'ev et al., "Electronic structure of silicon interfaces with amorphous and epitaxial insulating oxides Sc2O3, Lu2O3, LaLuO3", Microelectronic Engineering 84, (2007). pp. 2278-2281 (cited in specification).
Dai Hisamoto et al., "R&D Prospects of Si ULSI Devices", Hitachi Review Apr. 2007, vol. 89 No. 04 pp. 324-325 (cited in specification).
P. W. Peacock and J. Robertson, "Band offsets and Schottky barrier heights of high dielectric constant oxides", J. Appl. Phys., 92, pp. 4712-4721 (2002) (cited in specification).
Pieter Dorenbos, "A Review on How Lanthanide Impurity Levels Change with Chemistry and Structure of Inorganic Compounds", ECS Journal of Solid State Science and Technology 2 (2), pp. R3001-R3011, (2013) (cited in specification).
Extended European Search Report for corresponding EP Application No. 20813476.7 issued Jun. 27, 2022.

* cited by examiner

FIG. 2
(a)
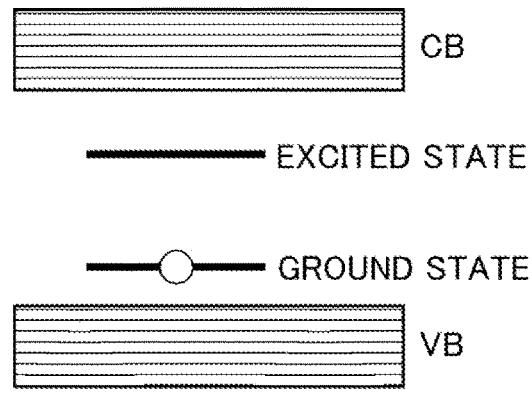
(b)
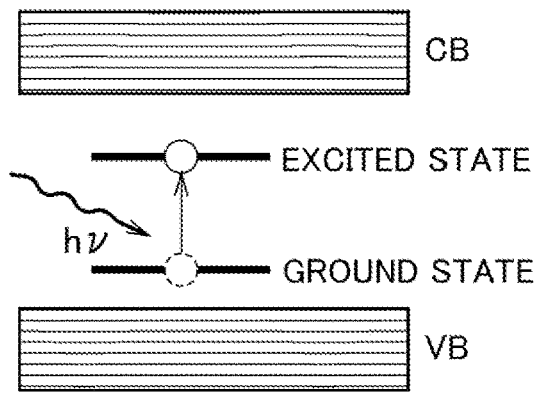
(c)
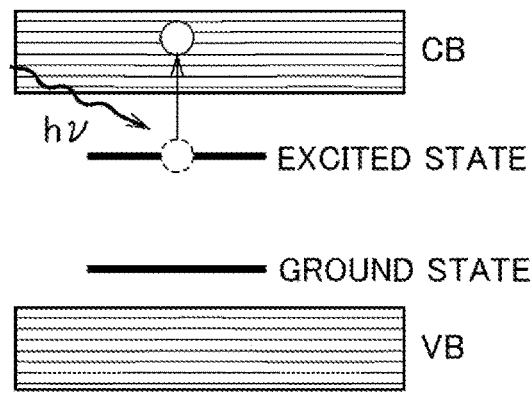

FIG. 12
(a)
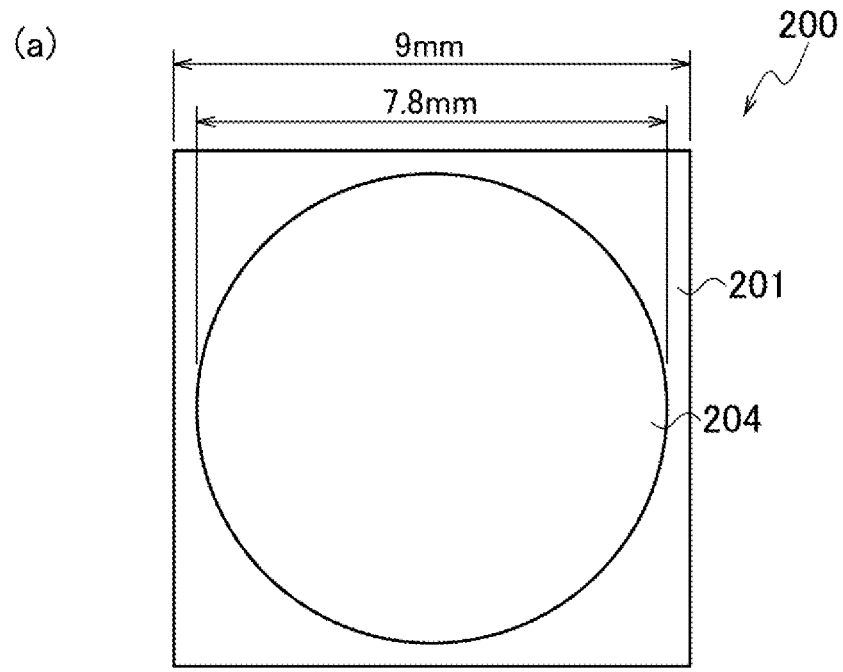
(b)
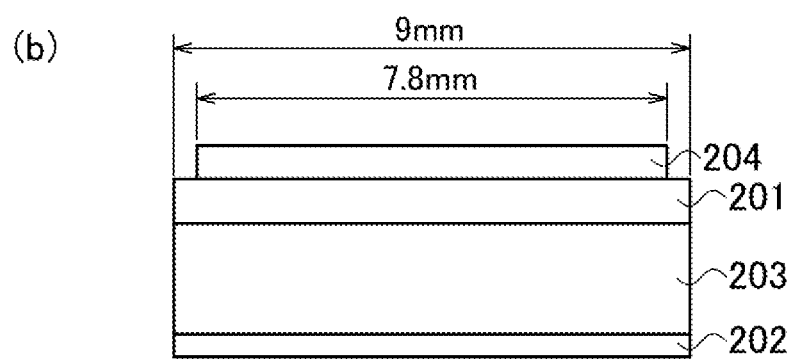

EXCITATION SPECTRUM / FLUORESCENCE SPECTRUM
OF INDOCYANINE GREEN (ICG) FLUOROCHROME

LIGHT-EMITTING DEVICE, AND ELECTRONIC DEVICE AND INSPECTION METHOD USING SAME

TECHNICAL FIELD

The present invention relates to a light emitting device, and an electronic device and an inspection method using the light emitting device.

BACKGROUND ART

There has been known a light emitting device including a combination of an excitation light source for emitting a laser beam and a wavelength converter including multiple kinds of phosphors. As a light emitting device having such a light source for emitting a laser beam, for example, a laser lighting device or a laser projector is known. The light emitting device having a light source for emitting a laser beam generally performs high light density excitation of phosphors.

In such a light emitting device, the intensity (luminance) of light emitted by a phosphor tends to increase as the energy density of a laser beam from an excitation light source increases. However, when the energy density of the laser beam exceeds a predetermined value, the intensity of the light emitted by the phosphor hardly increases. That is, a phenomenon occurs in which the output of the light emitted by the phosphor becomes saturated. Such an output saturation of fluorescence is believed to depend on the luminescence lifetime of a phosphor. Thus, a phosphor having a relatively long luminescence lifetime is considered to be difficult to emit fluorescence with a high intensity as compared with a phosphor having a short luminescence lifetime.

For this reason, Patent Literature 1 discloses a light source device that provides output light having high luminance and excellent color rendering properties by using a phosphor having a short luminescence lifetime. Specifically, it discloses a light source device including an excitation light source and a phosphor layer that emits fluorescence upon receiving excitation light from the excitation light source, wherein the phosphor layer includes a predetermined first phosphor and/or second phosphor, and the luminescence lifetimes of the first phosphor and the second phosphor are 0.1 ns or more and 250 ns or less.

CITATION LIST

Patent Literature

Patent Literature 1: International Publication No. WO 2018/163830

SUMMARY OF INVENTION

However, in the light emitting device using a laser beam, it is awaited to use not only a phosphor having a short luminescence lifetime but also a phosphor having a long luminescence lifetime to enhance the degree of freedom in wavelength selection of fluorescence emitted by the phosphor and the afterglow property of the fluorescence.

The present invention has been made in consideration of such an issue as described above, which is inherent in related art. An object of the present invention is to provide a light emitting device that prevents output saturation of fluorescence emitted by a phosphor even when the phosphor having a long luminescence lifetime is used, and an electronic device and an inspection method each using the light emitting device.

To solve the above issue, a light emitting device according to a first aspect of the present invention includes: a light source that emits a primary light having a light energy density exceeding 0.5 W/mm$^2$; and a first phosphor that absorbs the primary light to convert the primary light into a first wavelength-converted light having a wavelength longer than that of the primary light. The first phosphor includes a compound serving as a host, the compound being a simple oxide including one kind of metal element or a composite oxide including a plurality of different kinds of the simple oxide as an end member. When an energy conversion value at a peak wavelength of the primary light is E1 electron volts and an energy conversion value at a fluorescence peak wavelength of the first wavelength-converted light is E2 electron volts, a bandgap energy of a crystal of the simple oxide is larger than a sum of the E1 electron volts and the E2 electron volts.

An electronic device according to a second aspect of the present invention includes the light emitting device according to the first aspect.

An inspection method according to a third aspect of the present invention uses the light emitting device according to the first aspect.

A phosphor according to a fourth aspect of the present invention is a phosphor having a composition formula represented by a following general formula (I):

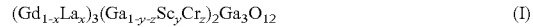

$$(Gd_{1-x}La_x)_3(Ga_{1-y-z}Sc_yCr_z)_2Ga_3O_{12} \qquad (I)$$

where x, y, and z satisfy $0 < x < 1$, $0 < y \leq 0.60$, $0 < z < 0.2$.

BRIEF DESCRIPTION OF DRAWINGS

FIG. 2 is a diagram illustrating energy levels for explaining an output saturation property of a phosphor.

FIG. 12 is a schematic diagram illustrating a wavelength conversion device for use in evaluation of the fluorescence output saturation property in example 1. FIG. 12(a) is a plan view of the wavelength conversion device, and FIG. 12(b) is a side view of the wavelength conversion device.

FIG. 19 is a graph for explaining a relative intensity of the excitation spectrum of the ICG at a fluorescence peak wavelength of a phosphor when the ICG absorption efficiency relative values is determined.

DESCRIPTION OF EMBODIMENTS

Figure 1:
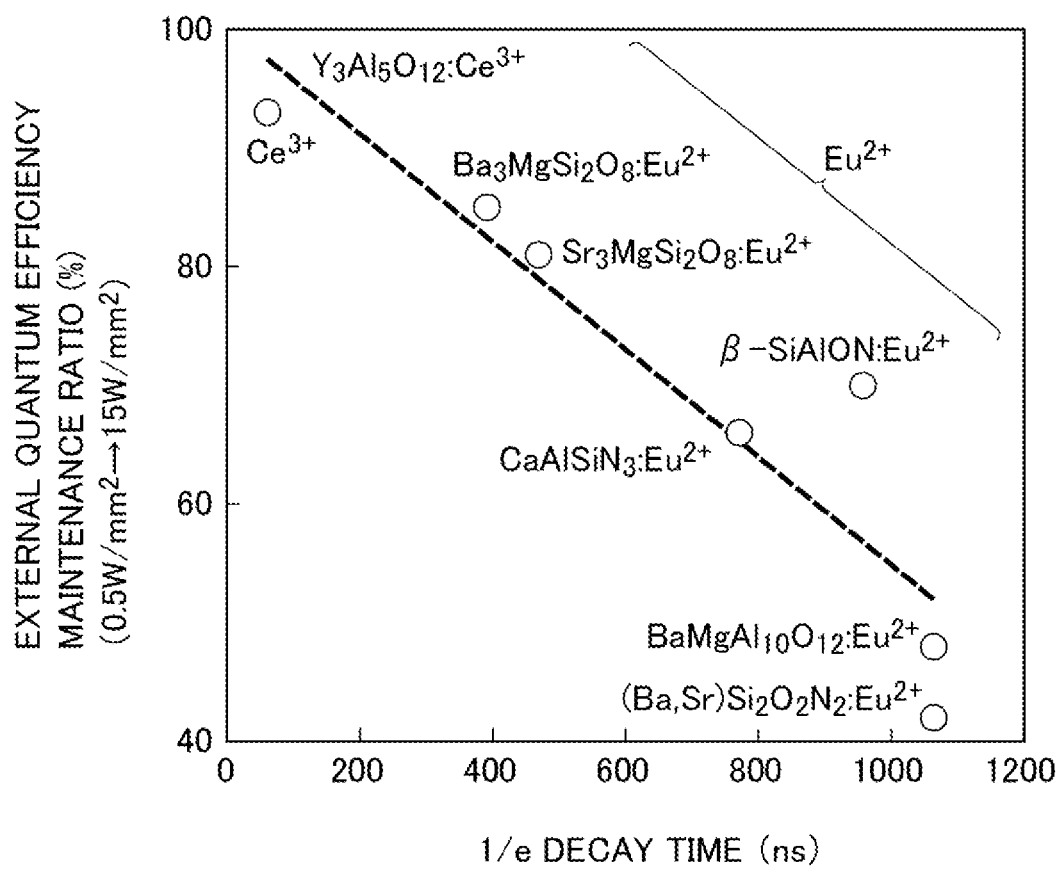
FIG. 1 is a graph illustrating a relationship between a fluorescence saturation property (external quantum efficiency maintenance ratio) and a luminescence lifetime (1/e decay time) in a Ce$^{3+}$-activated phosphor and an Eu$^{2+}$-activated phosphor.

Referring to the drawings, a description is given below of a light emitting device according to a present embodiment, and an electronic device and an inspection method each using the light emitting device. Note that dimensional ratios in the drawings are exaggerated for convenience of explanation and are sometimes different from actual ratios.

[Light Emitting Device]

In a light emitting device including a combination of a light source for emitting excitation light and a wavelength converter including a phosphor, the intensity (luminance) of fluorescence emitted by the phosphor usually increases as the energy of the excitation light increases. However, when the energy of the excitation light exceeds a predetermined value, the output of the fluorescence emitted by the phosphor becomes saturated, and the intensity of the fluorescence hardly increases. It is believed that such output saturation of the fluorescence emitted by the phosphor depends on the luminescence lifetime of the phosphor.

FIG. 1 illustrates a relationship between an external quantum efficiency maintenance ratio and a luminescence lifetime (1/e decay time) in a $Ce^{3+}$-activated phosphor and an $Eu^{2+}$-activated phosphor. The external quantum efficiency maintenance ratio is a ratio of the external quantum efficiency when a phosphor is irradiated with an excitation light having an energy density of 0.5 W/mm² to the external quantum efficiency when the phosphor is irradiated with an excitation light having an energy density of 15 W/mm². For the phosphor, the higher the external quantum efficiency maintenance ratio, the smaller the fluorescence output saturation. As illustrated in FIG. 1, it is seen that as the 1/e decay time, that is the luminescence lifetime, decreases, the external quantum efficiency maintenance ratio of the phosphor increases, and the fluorescence output saturation tends to decrease. Thus, it is considered that a phosphor having a relatively long luminescence lifetime has a larger fluorescence output saturation than a phosphor having a short luminescence lifetime and has a difficulty to emit light of high intensity.

The mechanism of such fluorescence output saturation is considered as follows. First, when a phosphor is irradiated with an excitation light having a wavelength corresponding to the absorption band inherent to the luminescent ion, an electron in the ground state of the luminescent ion illustrated in FIG. 2(a) rises to the excited state as illustrated in FIG. 2(b). When the electron is excited to a high excitation level, it usually undergoes nonradiative relaxation to the lowest excited singlet state by internal conversion and then returns to the ground state, at which time it emits fluorescence. Here, when an electron with a low transition probability absorbs more excitation light before relaxing from the excitation level to the ground level, an excited state absorption (ESA), in which the electron transits from the excitation level to a conduction band (CB), occurs, and photoionization occurs as illustrated in FIG. 2(c). Thus, when the transition probability of the electron is low, the excited state absorption occurs, and the relaxation from the lowest excited singlet state to the ground state is reduced, so that the intensity (luminance) of the fluorescence emitted by the phosphor is difficult to increase (see O. B. Shchekin et al., Phys. Status Solidi, RRL10 (2016), and A. Lenef et al., Proc. SPIE 8841, Current Developments in Lens Design and Optical Engineering XIV, 884107 (2013)).

Figure 3:
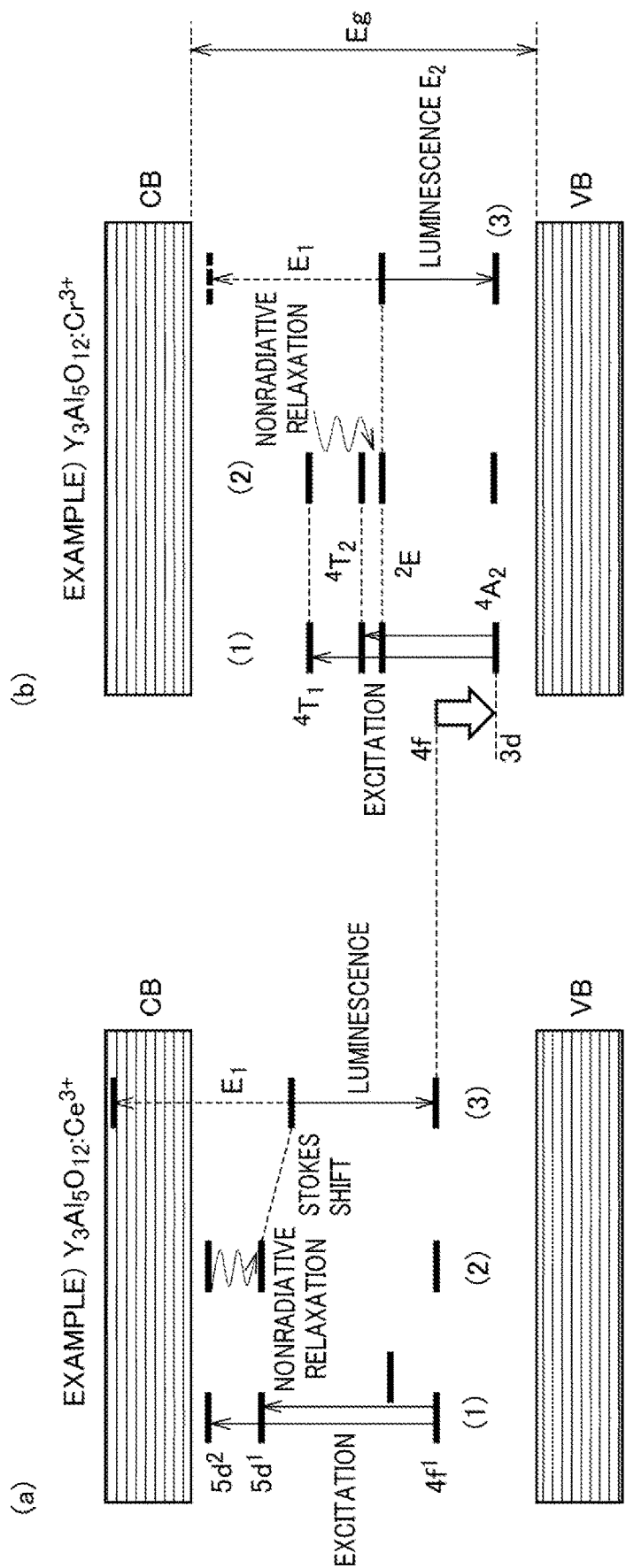
FIG. 3(a) is a diagram illustrating energy levels for explaining the output saturation property of Y$_3$Al$_5$O$_{12}$:Ce$^{3+}$ phosphor.
FIG. 3(b) is a diagram illustrating energy levels for explaining the output saturation property of Y$_3$Al$_5$O$_{12}$:Cr$^{3+}$ phosphor.

FIG. 3(a) illustrates energy levels of $Y_3Al_5O_{12}:Ce^{3+}$, which is a phosphor activated with a $Ce^{3+}$ ion having a short luminescence lifetime. FIG. 3(b) illustrates energy levels of $Y_3Al_5O_{12}:Cr^{3+}$, which is a phosphor activated with a $Cr^{3+}$ ion having a long luminescence lifetime. Note that the luminescence lifetime (1/e decay time) of the $Ce^{3+}$ ion is usually $10^{-9}$ to $10^{-8}$ seconds, and that of the $Cr^{3+}$ ion is usually $10^{-4}$ to $10^{-3}$ seconds.

As illustrated in FIG. 3(a), when the $Y_3Al_5O_{12}:Ce^{3+}$ phosphor is irradiated with excitation light, an electron in the ground state in the $Ce^{3+}$ ion rises to the excited state (see (1) in FIG. 3(a)). The electron in the excited state relaxes nonradiatively to the lowest excited singlet state by internal conversion (see (2) in FIG. 3(a)). After the Stokes shift, the electron relaxes from the excitation level to the ground level, at which time it emits fluorescence (see (3) in FIG. 3(a)). Here, the electron of the $Ce^{3+}$ ion has a high transition probability from the excitation level to the ground level and easily relaxes its energy. Thus, the excited state absorption (ESA) hardly occurs before relaxation from the excitation level to the ground level, and the fluorescence output saturation of the $Y_3Al_5O_{12}:Ce^{3+}$ phosphor decreases.

Similarly, when the $Y_3Al_5O_{12}:Cr^{3+}$ phosphor is irradiated with excitation light, as illustrated in FIG. 3(b), an electron in the ground state in the $Cr^{3+}$ ion rises to the excited state (see (1) in FIG. 3(b)). The electron in the excited state relaxes nonradiatively to the lowest excited singlet state by internal conversion (see (2) in FIG. 3(b)). Then, the electron relaxes from the excitation level to the ground level, at which time it emits fluorescence (see (3) in FIG. 3(b)). Here, the electron of the $Cr^{3+}$ ion has a low transition probability from the excitation level to the ground level and is difficult to relax its energy. Thus, the excitation light is further absorbed before relaxation from the excitation level to the ground level, and the excited state absorption easily occurs. As a result, the relaxation from the lowest excited singlet state to the ground state is reduced, and the fluorescence output saturation of the $Y_3Al_5O_{12}:Cr^{3+}$ phosphor increases.

Here, as illustrated in (3) of FIG. 3(b), an energy conversion value at a peak wavelength of the excitation light further absorbed by the electron in the lowest excited singlet state is E1 electron volts, and an energy conversion value at a fluorescence peak wavelength is E2 electron volts. The light energy is determined by formula 1 below.

$$E=h\nu=h\times c/\lambda \quad \text{[Formula 1]}$$

where h is Planck's constant, E is the energy of light, ν is the vibration frequency of light, c is the velocity of light, and λ is the wavelength of light.

When the energy E1 of the excitation light further absorbed by the electron in the lowest excited singlet state is small, the possibility of the transition from the excitation level to the conduction band (CB) is considered to be small. That is, when the sum (E1+E2) of the energy E1 at the peak wavelength of the excitation light and the energy E2 at the peak wavelength of the luminescence (fluorescence) is smaller than a bandgap energy (Eg) of the crystal constituting the host of the phosphor, the possibility of the excited state absorption is considered to be reduced.

Figure 4:
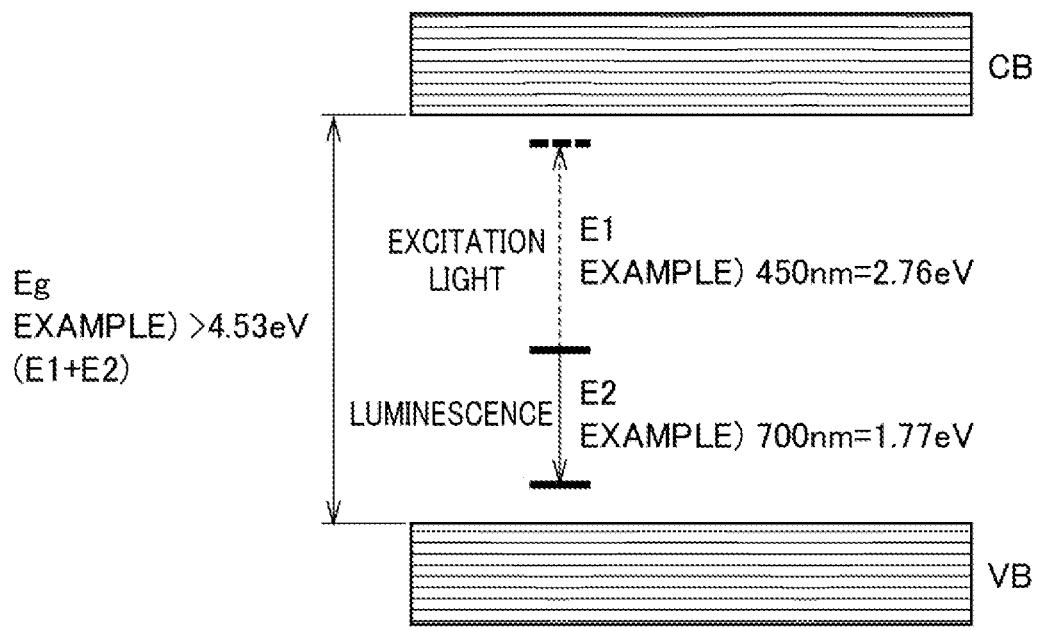
FIG. 4 is a diagram illustrating energy levels for explaining the output saturation property of a first phosphor used in a light emitting device according to the present embodiment.

Specifically, as illustrated in FIG. 4, when the fluorescence peak wavelength of the phosphor is 700 nm, the energy E2 of the fluorescence is 1.77 eV. When the peak wavelength of the excitation light for exciting the phosphor is 450 nm, the energy E1 of the excitation light is 2.76 eV. Thus, the sum (E1+E2) of the energy E1 of the excitation light and the energy E2 of the fluorescence is 4.53 eV. When the bandgap energy Eg of the host crystal constituting the phosphor exceeds 4.53 eV, the electron in the lowest excited singlet state hardly transitions to the conduction band (CB) even when it absorbs the excitation light, which reduces the possibility of the excited state absorption.

The light emitting device according to the present embodiment includes a light source that emits a primary light, which is excitation light, and a first phosphor that absorbs the primary light and converts it into a first wavelength-converted light (fluorescence) having a wavelength longer than that of the primary light. The excitation light and the phosphor are appropriately selected so that the sum (E1+E2) of the energy E1 of the excitation light and the energy E2 of the fluorescence is smaller than the bandgap energy Eg of the host crystal constituting the first phosphor.

As illustrated in FIGS. 5 to 8, the light emitting device 1, 1A, 1B, 1C according to the present embodiment includes at least a light source 2 that emits a primary light 6, and a wavelength converter 3, 3A including a first phosphor 4 that emits a first wavelength-converted light 7. In the light emitting device 1, 1A, 1B, 1C, when the primary light 6 emitted by the light source 2 enters the wavelength converter 3, 3A, the wavelength converter 3, 3A emits the first wavelength-converted light 7 that is fluorescence.

(Light Source)

The light source 2 is a light emitting element that emits the primary light 6. Preferably, the primary light 6 is a laser beam. This enables the light emitting device to have the first phosphor 4 to be irradiated with high density spot light, thereby easily having a point light source of high output and expanding the range of industrial use of solid-state lighting.

As the light source 2, for example, a laser element, such as a surface emitting laser diode, is used. The output energy of the laser beam emitted by one laser element is preferably 0.1 W or more, more preferably 1 W or more, still more preferably 5 W or more. The light energy density of the laser beam emitted by the light source 2 preferably exceeds 0.5 $W/mm^2$, more preferably 2 $W/mm^2$ or more, still more preferably 10 $W/mm^2$ or more. As described later, the phosphor in the wavelength converter 3, 3A is capable of wavelength-converting the high-output laser beam with high efficiency. Thus, the light energy density of the laser beam emitted by the light source 2 exceeding 0.5 $W/mm^2$ enables the light emitting device to emit high output near-infrared light.

The light source 2 provided in the light emitting device 1, 1A, 1B, 1C may be a light emitting diode (LED). For example, using an LED emitting light with an energy of 100 mW or more as the light source 2 enables the phosphor in the wavelength converter 3, 3A to be excited by high output light. This enables the light emitting device 1, 1A, 1B, 1C to emit high output near infrared light and to exhibit the same effect as when a laser element is used.

As described above, in the light emitting device 1, 1A, 1B, 1C, preferably, the light source 2 is at least one of a laser element or a light emitting diode. However, the light source 2 is not limited thereto, and any light emitting element is usable as long as it emits the primary light 6 having a high energy density. Specifically, preferably, the light source 2 is a light emitting element that emits the primary light 6 having a light energy density exceeding 0.5 $W/mm^2$. In this case, the light emitting device 1, 1A, 1B, 1C emits high output near-infrared light, which makes it possible to excite the phosphor in the wavelength converter 3, 3A with the high output light. Note that the energy density of the primary light 6 emitted by the light source 2 is more preferably 2 $W/mm^2$ or more, still more preferably 10 $W/mm^2$ or more. The upper limit of the light energy density of the primary light 6 emitted by the light source 2 is not limited but may be, for example, 50 $W/mm^2$.

Preferably, the primary light 6 emitted by the light source 2 is a violet light having an emission peak in a wavelength range of 380 nm to less than 435 nm, or a blue light having an emission peak in a wavelength range of 435 nm to less than 470 nm. Thus, a semiconductor light emitting element (light emitting diode or laser diode), which is easy to obtain and relatively inexpensive, is usable as the light source 2, and thus the light emitting device is advantageous for industrial production. Further, the phosphor in the wavelength converter 3, 3A is excited with high efficiency, which enables the light emitting device to emit high output near-infrared light.

The light source 2 may emit the primary light 6 having an emission peak in a wavelength range of 500 nm to 560 nm. Thus, the phosphor in the wavelength converter 3, 3A is excited by the high-output primary light 6, which enables the light emitting device to emit high-output near-infrared light.

The light source 2 may emit the primary light 6 having an emission peak in a wavelength range of 600 nm to 700 nm. This enables the phosphor in the wavelength converter 3, 3A to be excited by a red light of relatively low energy, which provides a light emitting device that emits high-output near-infrared light with less heat generation due to Stokes loss of the phosphor.

As described above, the types of the light source 2 provided in the light emitting device 1, 1A, 1B, 1C is not limited. However, the types of the light source 2 provided in the light emitting device 1, 1A, 1B, 1C are preferably three types or less, more preferably two types or less, still more preferably one type. Such a configuration is simple with few types of the light source 2, which provides the light emitting device 1, 1A, 1B, 1C that is compact.

Preferably, the light emitting device 1, 1A, 1B, 1C is provided with multiple light sources of the same type. Such a configuration enables the wavelength converter 3, 3A to be excited by light of stronger energy, which provides a light emitting device that emits near-infrared light of higher output.

(Wavelength Converter)

Figure 5:
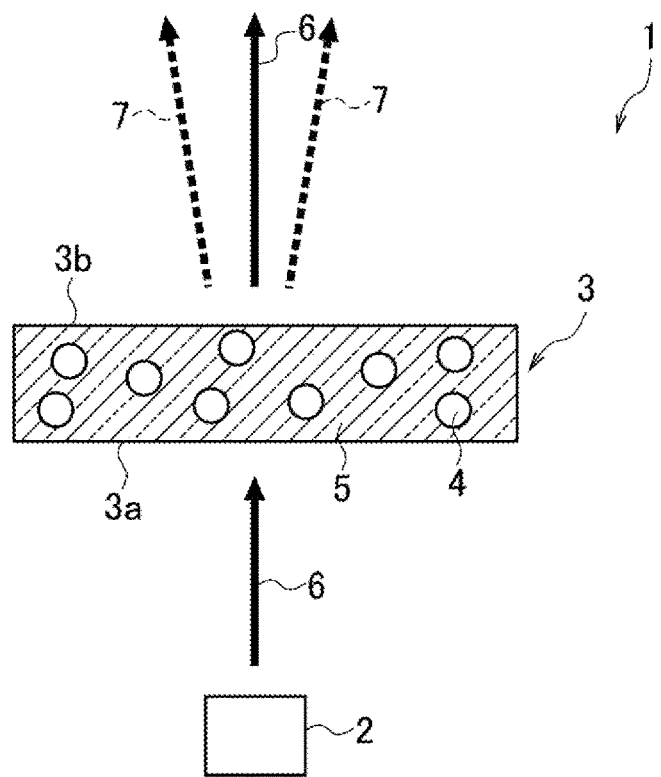
FIG. 5 is a schematic sectional view of an example of the light emitting device according to the present embodiment.
Figure 6:
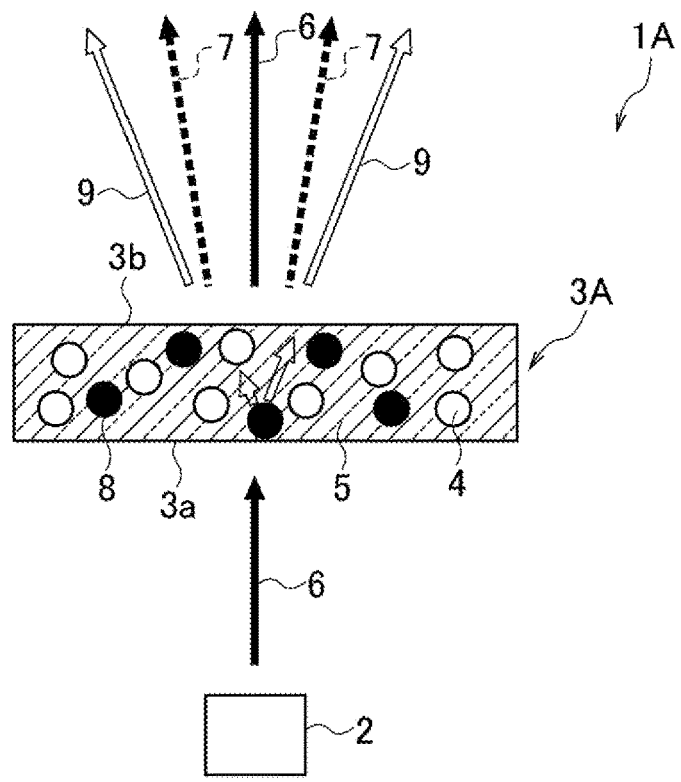
FIG. 6 is a schematic sectional view of another example of the light emitting device according to the present embodiment.
Figure 7:
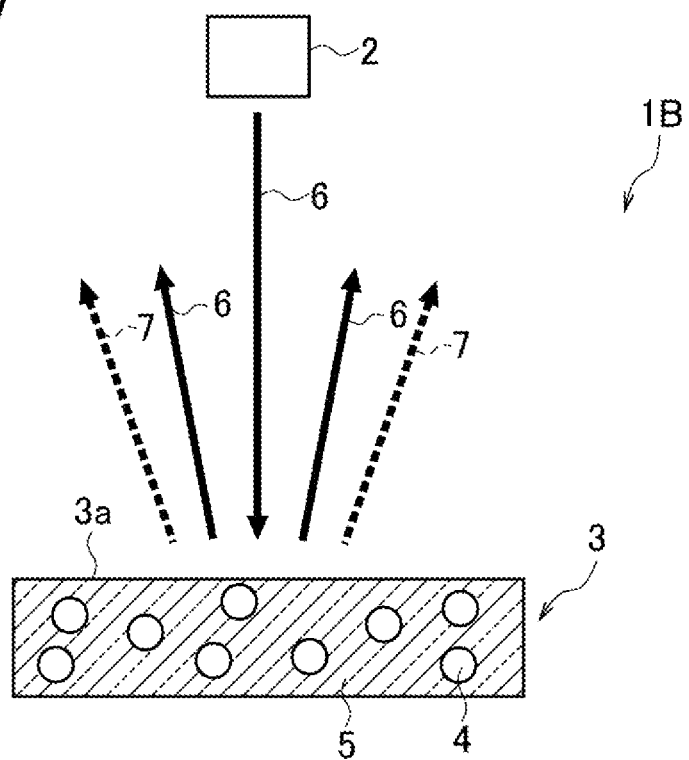
FIG. 7 is a schematic sectional view of another example of the light emitting device according to the present embodiment.
Figure 8:
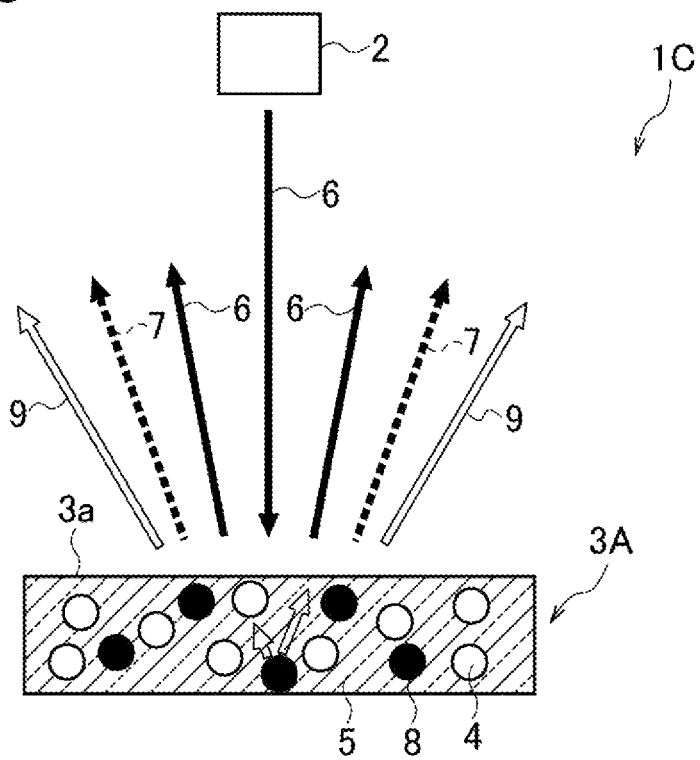
FIG. 8 is a schematic sectional view of another example of the light emitting device according to the present embodiment.

As illustrated in FIGS. 5 to 8, the wavelength converter 3, 3A emits fluorescence having a wavelength longer than that of the primary light 6 by receiving the primary light 6. The wavelength converter 3, 3A illustrated in FIGS. 5 and 6 is configured to receive the primary light 6 at a front 3a and emit fluorescence from a back 3b. In contrast, the wavelength converter 3, 3A illustrated in FIGS. 7 and 8 is configured to receive the primary light 6 at the front 3a and emit fluorescence from the same front 3a.

The wavelength converter 3, 3A includes the first phosphor 4 that absorbs the primary light 6 and converts it into the first wavelength-converted light 7 having a wavelength longer than that of the primary light 6. Preferably, a compound serving as a host of the first phosphor 4 is a simple oxide including one kind of metal element or a composite oxide including a plurality of different kinds of the simple oxide as an end member. Thus, the sum (E1+E2) of the energy E1 of the primary light 6 as the excitation light and the energy E2 of the first wavelength-converted light 7 emitted by the first phosphor 4 is easily made smaller than the bandgap energy Eg of the host crystal constituting the first phosphor 4.

The simple oxide constituting the host of the first phosphor 4 is not limited as long as E1+E2 is smaller than Eg. Preferably, the simple oxide is $Al_2O_3$, $Ga_2O_3$, $Sc_2O_3$, $Y_2O_3$, $La_2O_3$, $Gd_2O_3$, $Lu_2O_3$, $Eu_2O_3$, $Ho_2O_3$, $Er_2O_3$, $Tm_2O_3$, $ZrO_2$, or $HfO_2$, as illustrated in table 1, for example. Note that table 1 also illustrates the bandgap energy of the crystal of each simple oxide and a literature describing the bandgap energy.

TABLE 1

| Composition | Bandgap energy (eV) | Reference document |
|---|---|---|
| $Al_2O_3$ | 8.8 | John Robertson, "Band offsets of wide-band-gap oxides and implications for future electronic devices", J. Vac. Sci. Technol., B 18.3., 1785 (2000) |
| $Ga_2O_3$ | 4.8 | Masataka Higashiwaki, Kohei Sasaki, "Crystal Growth and Device Application of Gallium Oxide (Ga2O3)", Surface Science, Vol. 35, No. 2, pp. 102-107, (2014) |
| $Sc_2O_3$ | 6 | A. V. Emeline et al., "Photostimulated Generation of Defects and Surface Reactions on a Series of Wide Band Gap Metal-Oxide Solids", The Journal of Physical Chemistry, B 103, (43), 9190-9199 |
| $Y_2O_3$ | 5.8 | Fiscal year Heisei 26 (2014) TSUBAME Industrial Application Trial Use Results Report |
| $La_2O_3$ | 6.1 | Keisuke Kobayashi, "Gate dielectric film evaluation by Soft X-ray Photoelectron Spectroscopy", SPring-8 Industrial Application Promotion Office, Internet <URL: http://support.spring8.or.jp/Doc_lecture/PDF_030305/ulsi_7.pdf> |
| $Gd_2O_3$ | 5.6 | Japanese Patent No. 4575362, paragraph [0002] |
| $Lu_2O_3$ | 5.4 | "Electronic structure of silicon interfaces with amorphous and epitaxial insulating oxides: $Sc_2O_3$, $Lu_2O_3$, $LaLuO_3$", Microelectronic Engineerinzg, 84, (2007), 2278-2281 |
| $Eu_2O_3$ | ≥5.0 | Dai Hisamoto, et al. "R&D Prospects of Si ULSI Devices", Hitachi Review April 2007, Vol. 89 No. 04 324-325, Internet <http://www.hitachihyoron.com/jp/pdf/2007/04/2007_04_01.pdf> |
| $Ho_2O_3$ | | |
| $Er_2O_3$ | | |
| $Tm_2O_3$ | | |
| $ZrO_2$ | 5.8 | P. W. Peacock and J. Robertson, "Band offsets and Schottky barrier heights of high dielectric constant oxides", |
| $HfO_2$ | 5.8 | J. Appl. Phys., 92, p. 4712 (2002) |

The composite oxide constituting the host of the first phosphor 4 is not limited as long as E1+E2 is smaller than Eg. Preferably, the composite oxide is an oxide obtained by arbitrary composition of at least two simple oxides selected from the group consisting of $Al_2O_3$, $Ga_2O_3$, $Sc_2O_3$, $Y_2O_3$, $La_2O_3$, $Gd_2O_3$, $Lu_2O_3$, $Eu_2O_3$, $Ho_2O_3$, $Er_2O_3$, $Tm_2O_3$, $ZrO_2$, and $HfO_2$. Table 2 illustrates bandgap energy of a crystal of each composite oxide and a document describing the bandgap energy. As far as the inventor of the present invention has investigated, any of the composite oxides including a simple oxide having a large bandgap energy of a crystal as an end member tends to have a high bandgap energy. For example, a composite oxide including a simple oxide having a bandgap energy of a crystal of 4.6 eV or more as an end member tends to have a bandgap energy of a crystal of 4.6 eV or more. Thus, preferably, the composite oxide constituting the host of the first phosphor 4 includes a simple oxide having a large bandgap energy as an end member.

TABLE 2

| Composition | Bandgap energy (eV) | Reference document |
|---|---|---|
| $Y_3Al_5O_{12}$ | 7.6 | Pieter Dorenbos, "A Review on How Lanthanide Impurity |
| $Y_3Ga_5O_{12}$ | 6.5 | Levels Change with Chemistry and Structure of Inorganic |
| $Gd_3Ga_5O_{12}$ | 6.4 | Compounds", ECS Journal of Solid State Science and |
| $LaAlO_3$ | 6.3 | Technology, 2 (2), R3001-R3011, (2013) |
| $YAlO_3$ | 8.5 | Reading from the graph in FIG. 22 |
| $LuAlO_3$ | 8.9 | |

Preferably, the bandgap energy Eg of the crystal of the simple oxide serving as the host of the first phosphor 4 is 4.6 eV or more. For example, when $Cr^{3+}$ is used as an activator of the first phosphor 4, the emission peak wavelength of the first phosphor 4 is about 690 nm or more. For the excitation light (primary light 6) emitted by the light source 2, a blue light having a peak wavelength of 450 nm is generally used. Thus, the energy E1 at the peak wavelength of the excitation light becomes 2.756 eV, the energy E2 at the peak wavelength of the luminescence (fluorescence) becomes 1.797 eV or less, and the sum of E1 and E2 becomes 4.553 eV or less. Thus, by using a compound having a bandgap energy Eg of a crystal of 4.6 eV or more as the host of the first phosphor 4, it is easy to make a phosphor difficult to have saturation of fluorescence.

Preferably, the first phosphor 4 includes at least one element selected from the group consisting of aluminum (Al), gallium (Ga), and scandium (Sc) in a crystal of a compound serving as a host. In the crystal of the host compound, $Al^{3+}$, $Ga^{3+}$, and $Sc^{3+}$ each have a size close to that of $Cr^{3+}$, which is an activator. That is, $Al^{3+}$ has an ionic radius of 0.675 Å in six-coordination, $Ga^{3+}$ has an ionic radius of 0.62 Å in six-coordination, $Sc^{3+}$ has an ionic radius of 0.745 Å in six-coordination, and $Cr^{3+}$ has an ionic radius of 0.615 Å in six-coordination. Thus, $Al^3$, $Ga^{3+}$ and $Sc^{3+}$ are easily partially replaced by $Cr^{3+}$ in the crystal of the host compound. Further, the ionic radius of $Cr^{3+}$ is smaller than those of $Al^{3+}$, $Ga^{3+}$, and $Sc^{3+}$, which acts to reduce the crystal field acting on $Cr^{3+}$ in the partially substituted crystal. Thus, a broad fluorescence spectrum is easily obtained, which provides a light emitting device advantageous for medical lighting using a fluorescence imaging method or a photodynamic therapy (PDT method).

As the activator included in the first phosphor 4, an element having a long luminescence lifetime is usable. As described above, making the sum of the energy E1 of the primary light 6 and the energy E2 of the first wavelength-converted light 7 smaller than the bandgap energy Eg of the host crystal of the first phosphor 4 prevents the saturation of fluorescence output and increases the intensity of the fluorescence emitted by the phosphor. Thus, not only an element having a short luminescence lifetime but also an element having a long luminescence lifetime is suitably usable as the activator. As the activator included in the first phosphor 4, an element having a 1/e decay time of $10^{-4}$ seconds or more is usable. Preferably, such an activator is at least one selected from the group consisting of $Cr^{3+}$, $V^{2+}$, $Mn^{4+}$, and $Fe^{5+}$.

Note that as the activator included in the first phosphor 4, an element having a short luminescence lifetime is also usable. Specifically, the activator included in the first phosphor 4 may be at least one of $Ce^{3+}$ having a 1/e decay time of $10^{-9}$ to $10^{-8}$ seconds, or $Eu^{2+}$ having a 1/e decay time of $10^{-7}$ to $10^{-6}$ seconds.

Preferably, the first wavelength-converted light 7 emitted by the first phosphor 4 includes fluorescence based on an electron energy transition of a transition metal ion, and the transition metal ion is $Cr^{3+}$. That is, preferably, the first phosphor 4 is a $Cr^{3+}$-activated phosphor. $Cr^{3+}$ has a mechanism of light absorption and luminescence based on a d-d transition. Thus, the wavelength of absorption and luminescence changes depending on the host crystal in which $Cr^{3+}$ is activated. Thus, selecting an appropriate host crystal with $Cr^{3+}$ as the luminescence center provides a light emitting device in which the spectral distribution in the wavelength range from red to near infrared is easily customized depending on the application. Moreover, the $Cr^{3+}$-activated phosphor is capable of converting a laser beam having a high energy density into near-infrared light with high efficiency. Thus, using the $Cr^{3+}$-activated phosphor provides a light emitting device that emits near-infrared light of higher output.

In the first phosphor 4, preferably, the cation element in the crystal of the compound serving as a host is made from only an element with a valence of three. Cr as an activator may take the valence of not only $Cr^{3+}$, but also $Cr^{2+}$ and $Cr^{4+}$. When there is a mixture in the valence of Cr in the first phosphor 4, the first phosphor 4 may act to reduce the efficiency of luminescence of near-infrared light by $Cr^{3+}$. Thus, having the cation element of only an element with a valence of three in the host crystal prevents Cr from having a valence of $Cr^{2+}$ or $Cr^{4+}$ and provides a light emitting device capable of high output. Moreover, the oxide of the trivalent cation element has a wide bandgap energy Eg, which provides a light emitting device hardly causing saturation of fluorescence output.

Preferably, the first phosphor 4 includes two or more kinds of $Cr^{3+}$-activated phosphors. This makes it possible to control the spectral distribution of the output light component in at least the near-infrared wavelength range. Thus, it is possible to obtain a light emitting device in which the spectral distribution is easily adjusted depending on the application utilizing a near-infrared fluorescent component.

Preferably, the first phosphor 4 has a garnet crystal structure. Also preferably, the first phosphor 4 is an oxide phosphor with a garnet crystal structure. The phosphor with a garnet structure, especially the oxide phosphor, has a polyhedral particle shape close to a sphere and has excellent dispersibility of a phosphor particle group. Thus, when the phosphor included in the wavelength converter 3, 3A has a garnet structure, the wavelength converter excellent in light transmission is manufactured relatively easily, which enables higher output of the light emitting device. Further, since the phosphor with a garnet crystal structure has results as a phosphor for LEDs, the light emitting device that is highly reliable is obtained when the first phosphor 4 has the garnet crystal structure.

Preferably, the first phosphor 4 is a phosphor having a composition formula represented by the following general formula (I):

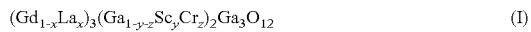

$$(Gd_{1-x}La_x)_3(Ga_{1-y-z}Sc_yCr_z)_2Ga_3O_{12} \quad (I)$$

Note that in formula (I), x, y, and z satisfy $0<x<1$, $0<y\leq0.60$, $0<z<0.2$.

The phosphor represented by the general formula (I) is a phosphor having $(Gd_{1-x}La_x)_3(Ga_{1-y-z}Sc_y)_2Ga_3O_{12}$ as a host and using $Cr^{3+}$ as an activator. $(Gd_{1-x}La_x)_3(Ga_{1-y-z}Sc_y)_2Ga_3O_{12}$ is a composite oxide including $Gd_2O_3$, $La_2O_3$, $Ga_2O_3$, and $Sc_2O_3$, which are simple oxides with one metal element, as end members. From table 1, the bandgap energy of $Gd_2O_3$ is 5.6 eV, the bandgap energy of $La_2O_3$ is 6.1 eV, the bandgap energy of $Ga_2O_3$ is 4.8 eV, and the bandgap energy of $Sc_2O_3$ is 6.0 eV. As far as the inventor of the present invention has investigated, any of the composite oxides including a simple oxide having a large bandgap energy of a crystal as an end member tends to have a high bandgap energy. Thus, the bandgap energy of the crystal of $(Gd_{1-x}La_x)_3(Ga_{1-y-z}Sc_y)_2Ga_3O_{12}$ is estimated to be 4.8 eV or more.

The phosphor represented by general formula (I) uses $Cr^{3+}$ as an activator, so that a laser beam having a high energy density is converted into a near-infrared light with high efficiency, and the fluorescence output is hardly saturated even when a laser beam is used. Thus, it is possible to obtain a light emitting device that emits a high output near-infrared light. Furthermore, by using $(Gd_{1-x}La_x)_3(Ga_{1-y-z}Sc_y)_2Ga_3O_{12}$ as a host compound, it becomes possible to emit fluorescence having a large amount of a light component near 770 nm.

In general formula (I) of the first phosphor 4, more preferably, x satisfies $0.05\leq x\leq0.25$. In general formula (I), y more preferably satisfies $0.06\leq y\leq0.60$, still more preferably $0.20\leq y\leq0.60$, and particularly preferably $0.20\leq y\leq0.50$. Having x and y in general formula (I) within this range enhances the efficiency of absorption of near-infrared light by a fluorescent drug used in the fluorescence imaging method. Thus, using a phosphor represented by general formula (I) as the first phosphor 4 provides a light emitting device suitable for the fluorescence imaging method.

Preferably, the first wavelength-converted light 7 emitted by the first phosphor 4 is a near-infrared light having a fluorescence peak within a wavelength range of 700 nm to less than 1000 nm. Light in a wavelength range of 650 nm to less than 1400 nm is particularly easily transmitted through a living body, and the wavelength range is generally called a "biological window". Since the first wavelength-converted light 7 is near-infrared light, the light emitting device advantageous for medical application is provided because the light is easily introduced from the outside to the inside of the body. The first wavelength-converted light 7 is a low energy light having the energy conversion value E2 of less than 1.77 eV and 1.24 eV or more. Thus, even when the primary light 6 is a high energy violet light (380 nm or more and less than 435 nm: less than 3.26 eV and 2.85 eV or more), the sum of E1 and E2 is less than 5.03 eV and 4.09 or more. Thus, the use of phosphors based on orthodox oxides and composite oxides having high industrial results is easy, and the selection range of phosphors is widened, so that the light emitting device is advantageous for industrial production.

The first wavelength-converted light 7 preferably has a fluorescence peak in a wavelength range exceeding 750 nm, more preferably has a fluorescence peak in a wavelength range exceeding 770 nm. As a result, the near-infrared light emitted by the light emitting device 1, 1A, 1B, 1C is more easily transmitted through the living body, which provides a near-infrared light emitting device suitable for medical lighting applications.

Preferably, the first wavelength-converted light 7 has a light component over the entire wavelength range of at least 700 nm to 800 nm. This results in a configuration in which a drug used in the fluorescence imaging method or the photodynamic therapy efficiently absorbs the light component of the first wavelength-converted light 7, as is described later. Further, the configuration is adapted to various kinds of drugs having different light absorption properties.

More preferably, the first wavelength-converted light 7 has an optical component over the entire wavelength range of at least 750 nm to 800 nm. Also preferably, the first wavelength-converted light 7 has a light component over the entire wavelength range of 600 nm to 800 nm. This results in a configuration in which a drug used in the fluorescence imaging method or the photodynamic therapy efficiently absorbs the light component of the first wavelength-converted light 7. Further, the configuration is adapted to various kinds of drugs having different light absorption properties.

As illustrated in FIG. 5, in addition to the first phosphor 4, preferably, the wavelength converter 3 further includes a sealing material 5 that disperses the first phosphor 4. Preferably, the wavelength converter 3 has the first phosphor 4 dispersed in the sealing material 5. By dispersing the first phosphor 4 in the sealing material 5, the primary light 6 emitted by the light source 2 is efficiently absorbed and wavelength-converted into a near-infrared light. Further, the wavelength converter 3 is easily formed into a sheet shape or a film shape.

Preferably, the sealing material 5 is at least one of an organic material or an inorganic material, particularly at least one of a transparent (translucent) organic material or a transparent (translucent) inorganic material. Examples of the sealing material of the organic material include a transparent organic material, such as a silicone resin. Examples of the sealing material of the inorganic material include a transparent inorganic material, such as a low melting point glass.

As illustrated in FIG. 5, the wavelength converter 3 includes the first phosphor 4 that emits the first wavelength-converted light 7. However, as illustrated in FIGS. 6 and 8, preferably, the wavelength converter further includes a second phosphor 8 that absorbs the primary light 6 emitted by the light source 2 and emits a second wavelength-converted light 9 that is visible light. In other words, preferably, the light emitting device 1A, 1C further includes the second phosphor 8 that absorbs the primary light 6 and converts it into the second wavelength-converted light 9 that has a wavelength longer than that of the primary light 6 and is different from the first wavelength-converted light 7. Appropriately combining multiple kinds of arbitrary phosphors enables the shape of the fluorescence spectrum and the excitation property to be controlled, which provides the light emitting device 1A, 1C in which the spectral distribution of the output light is easily adjusted according to the application. Providing the wavelength converter 3A with the second phosphor 8 enables the wavelength converter 3A to emit a white output light by additive color mixing of the primary light 6 emitted by the light source 2, for example, a blue laser beam, and the second wavelength-converted light 9.

The second phosphor 8 included in the wavelength converter 3A is not limited as long as it absorbs the primary light 6 emitted by the light source 2 and emits the second wavelength-converted light 9 that is visible light. Preferably, the second phosphor 8 is a $Ce^{3+}$-activated phosphor having, as a host, a compound having, as a main component, at least one selected from the compound group consisting of a garnet type crystal structure, a calcium ferrite type crystal structure, and a lanthanum silicon nitride ($La_3Si_6N_{11}$) type crystal structure. Preferably, the second phosphor 8 is a $Ce^{3+}$-activated phosphor having, as a host, at least one compound selected from the compound group consisting of a garnet type crystal structure, a calcium ferrite type crystal structure, and a lanthanum silicon nitride type crystal structure. Using the above-described second phosphor 8 provides output light with a large amount of a light component from green to yellow.

Specifically, preferably, the second phosphor 8 is a $Ce^{3+}$-activated phosphor having, as a host, a compound (B) having, as a main component, at least one selected from the group consisting of $M_3RE_2(SiO_4)_3$, $RE_3Al_2(AlO_4)_3$, $MRE_2O_4$, and $RE_3Si_6N_{11}$.

Preferably, the second phosphor 8 is a $Ce^{3+}$-activated phosphor having, as a host, at least one selected from the group consisting of $M_3RE_2(SiO_4)_3$, $RE_3Al_2(AlO_4)_3$, $MRE_2O_4$, and $RE_3Si_6Ni_1$. Preferably, the second phosphor 8 is a $Ce^{3+}$-activated phosphor having, as a host, a solid solution having the compound (B) as an end member. Note that M is an alkaline-earth metal, and RE is a rare-earth element.

The above-described second phosphor 8 well absorbs a light in a wavelength range of 430 nm to 480 nm and converts it to a green to yellow light having a maximum intensity value in a wavelength range of 540 nm to 590 nm with high efficiency. Thus, a visible light component is easily obtained by using such a phosphor as the second phosphor 8.

Preferably, the wavelength converter 3, 3A is made from an inorganic material. Here, the inorganic material means materials other than organic materials and includes ceramics and metals as a concept. When the wavelength converter 3, 3A is made from an inorganic material, the wavelength converter 3, 3A has the thermal conductivity higher than that of the wavelength converter including an organic material, such as a sealing resin, thereby facilitating the heat radiation design. Thus, the temperature rise of the wavelength converter 3, 3A is effectively prevented even when the phosphor is photoexcited with high density by the primary light 6 emitted by the light source 2. As a result, the thermal quenching of the phosphor in the wavelength converter 3, 3A is prevented, and thus higher output of luminescence is possible.

As described above, the wavelength converter 3, 3A is preferably made from an inorganic material, and thus the sealing material 5 is preferably made from an inorganic material. Preferably, zinc oxide (ZnO) is used as the inorganic material of the sealing material 5. This further enhances the heat radiation of the phosphor, which prevents the output of the phosphor from decreasing due to thermal quenching and provides the light emitting device that emits a high output near-infrared light.

The wavelength converter 3, 3A may be a wavelength converter that does not use the sealing material 5. In this case, the wavelength converter 3, 3A may be made of only a phosphor. The wavelength converter 3, 3A may be formed by fixing particles of a phosphor to each other using an organic or inorganic binder. As the binder, a commonly used resin-based adhesive, ceramic fine particles, low melting point glass, or the like is usable. The wavelength converter not using the sealing material 5 is made thin, and thus it is suitably usable for the light emitting device.

Next, the operation of the light emitting device according to the present embodiment is described. In the light emitting device 1 in FIG. 5, first, the front 3a of the wavelength converter 3 is irradiated with the primary light 6 emitted by the light source 2. The primary light 6 emitted passes through the wavelength converter 3. When the primary light 6 passes through the wavelength converter 3, the first phosphor 4 included in the wavelength converter 3 absorbs a part of the primary light 6 and emits the first wavelength-converted light 7. In this way, a light including the primary light 6 and the first wavelength-converted light 7 is emitted from the back 3b of the wavelength converter 3 as output light.

In the light emitting device 1A in FIG. 6, first, the front 3a of the wavelength converter 3A is irradiated with the primary light 6 emitted by the light source 2. The primary light 6 emitted passes through the wavelength converter 3A. When the primary light 6 passes through the wavelength converter 3A, the second phosphor 8 included in the wavelength converter 3A absorbs a part of the primary light 6 and emits the second wavelength-converted light 9. Further, the first phosphor 4 included in the wavelength converter 3A absorbs a part of the primary light 6 and emits the first wavelength-converted light 7. In this way, a light including the primary light 6, the first wavelength-converted light 7, and the second wavelength-converted light 9 is emitted from the back 3b of the wavelength converter 3A as output light.

In the light emitting device 1B in FIG. 7, first, the front 3a of the wavelength converter 3 is irradiated with the primary light 6 emitted by the light source 2. Most of the primary light 6 enters the wavelength converter 3 from the front 3a of the wavelength converter 3, and the rest is reflected by the front 3a. In the wavelength converter 3, the first phosphor 4 excited by the primary light 6 emits the first wavelength-converted light 7, and the first wavelength-converted light 7 is emitted from the front 3a.

In the light emitting device 1C in FIG. 8, first, the front 3a of the wavelength converter 3A is irradiated with the primary light 6 emitted by the light source 2. Most of the primary light 6 enters the wavelength converter 3A from the front 3a of the wavelength converter 3A, and the rest is reflected by the front 3a. In the wavelength converter 3A, the second phosphor 8 excited by the primary light 6 emits the second wavelength-converted light 9, and the first phosphor 4 excited by the primary light 6 emits the first wavelength-converted light 7. Then, the first wavelength-converted light 7 and the second wavelength-converted light 9 are emitted from the front 3a.

In the light emitting device according to the present embodiment, the sum of the energy E1 of the excitation light emitted by the light source 2 and the energy E2 of the fluorescence emitted by the first phosphor 4 is smaller than the bandgap energy Eg of the host crystal constituting the first phosphor 4. Thus, even when the excitation light having a high light energy density is emitted, the possibility that the electron of the activator transits from the excitation level to the conduction band (CB) is reduced. Therefore, even when a phosphor having a long luminescence lifetime is used as the first phosphor 4, the output saturation of the fluorescence emitted by the phosphor is prevented and the intensity (luminance) of the light emitted by the phosphor is increased.

Thus, the light emitting device 1, 1A, 1B, 1C according to the present embodiment is provided with the light source 2 that emits the primary light 6 having a light energy density exceeding 0.5 W/mm$^2$, and the first phosphor 4 that absorbs the primary light 6 and converts it into the first wavelength-converted light 7 having a wavelength longer than that of the primary light 6. The host compound of the first phosphor 4 is a simple oxide including one kind of metal element or a composite oxide including a plurality of different kinds of the simple oxides as an end member. When the energy conversion value at the peak wavelength of the primary light 6 is E1 electron volts and the energy conversion value at the fluorescence peak wavelength of the first wavelength-converted light 7 is E2 electron volts, the bandgap energy Eg of the crystal of the simple oxide is larger than the sum of E1 and E2. The light emitting device uses, as the host compound of the first phosphor 4, a compound that hardly causes a phenomenon in which electrons in excited state in an activator are excited to the conduction band of the host compound and are inactivated, even when the energy of the primary light 6 is added to the excited electrons at a high density. Thus, even when a long-afterglow phosphor having a property of hardly relaxing energy from an excited state to a ground state is used, the light emitting device has a small fluorescence output saturation (phenomenon in which the fluorescence intensity of a phosphor is saturated when the density of light to be emitted to the phosphor is increased).

Preferably, the light emitting device 1, 1A, 1B, 1C according to the present embodiment is a medical light source or a medical lighting device. The light emitting device 1, 1A, 1B, 1C emits broad near-infrared light at high output to excite a fluorescent drug or a photosensitive drug taken into a living body through the "biological window". Thus, using the light emitting device 1, 1A, 1B, 1C as a medical light source or a medical lighting device makes the fluorescent drug and the photosensitive drug fully functional and provides a large therapeutic effect.

The light emitting device 1, 1A, 1B, 1C according to the present embodiment may be used for optical coherence tomography (OCT) or the like. Preferably, the light emitting device 1, 1A, 1B, 1C is a medical light emitting device used in a fluorescence imaging method or a photodynamic therapy. The fluorescence imaging method and the photodynamic therapy are a promising medical technology with a wide range of applications and are highly practical. The light emitting device 1, 1A, 1B, 1C illuminates the inside of the living body with a broad near-infrared high output light through the "biological window" and makes the fluorescent drug or the photosensitive drug taken into the living body fully functional, which is expected to have a large therapeutic effect.

The fluorescence imaging method is a method of observing a lesion by administering a fluorescent drug that selectively binds to the lesion, such as a tumor, to a subject, exciting the fluorescent drug with a specific light, and detecting and imaging fluorescence emitted by the fluorescent drug with an image sensor. The fluorescence imaging method makes it possible to observe lesions that are difficult to observe using only general lighting. As the fluorescent drug, a drug that absorbs excitation light in the near-infrared range, and emits fluorescence in the near-infrared range and at a wavelength longer than that of the excitation light is usable. Examples of the fluorescent drug used include at least one selected from the group consisting of indocyanine green (ICG), a phthalocyanine-based compound, a talaporfin sodium-based compound, and a dipicolylcyanine (DIPCY)-based compound.

The photodynamic therapy is a treatment method of administering a photosensitive drug that selectively binds to a target biological tissue to a subject and irradiating the photosensitive drug with near-infrared light. When the photosensitive drug is irradiated with the near-infrared light, the photosensitive drug generates active oxygen, which is usable to treat lesions, such as tumors or infections. Examples of the photosensitive drug used include at least one selected from the group consisting of a phthalocyanine-based compound, a porphyrin-based compound, a chlorin-based compound, a bacteriochlorin-based compound, a psoralen-based compound, a porfimer sodium-based compound, and a talaporfin sodium-based compound.

The light emitting device 1, 1A, 1B, 1C according to the present embodiment may be used also as a light source for a sensing system or a lighting system for a sensing system. In the light emitting device 1, 1A, 1B, 1C, it is possible to configure a highly-sensitive sensing system by using an orthodox light receiving element having light receiving sensitivity in the near-infrared wavelength range. This provides a light emitting device that facilitates miniaturization of the sensing system and broadening of the sensing range.

In the present embodiment, preferably, the phosphor (first phosphor) is a phosphor having a composition formula represented by the following general formula (I):

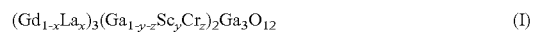

$$(Gd_{1-x}La_x)_3(Ga_{1-y-z}Sc_yCr_z)_2Ga_3O_{12} \qquad (I)$$

In formula (I), x, y, and z satisfy $0<x<1$, $0<y\leq0.60$, $0<z<0.2$.

Such a phosphor uses $Cr^{3+}$ as an activator, so that a laser beam having a high energy density is converted into a near-infrared light with high efficiency, and the fluorescence output is hardly saturated even when a laser beam is used. Furthermore, the phosphor emits fluorescence having a large amount of a light component near 770 nm, which provides a light emitting device suitable for, for example, the fluorescence imaging method.

Note that the phosphor represented by general formula (I) is suitably usable for the light emitting device 1, 1A, 1B, 1C, but the light emitting device is not limited thereto. That is, the phosphor represented by general formula (I) is usable in any light emitting device that emits near-infrared light by wavelength-converting the primary light. In other words, the light emitting device may include a phosphor represented by general formula (I). Such a light emitting device is usable in any medical device that emits near-infrared light. In other words, the medical device may include a light emitting device including a phosphor represented by general formula (I).

[Electronic Device]

Next, an electronic device according to the present embodiment is described. The electronic device according to the present embodiment includes one of the light emitting devices 1, 1A, 1B, and 1C according to the present embodiment. As described above, the light emitting device 1, 1A, 1B, 1C is expected to have a large therapeutic effect, and it is easy to miniaturize the sensing system. Since the electronic device according to the present embodiment includes the above-described light emitting device, a large therapeutic effect, miniaturization of the sensing system, and the like are expected when it is used for a medical device or a sensing device.

The electronic device includes, for example, the light emitting device 1, 1A, 1B, 1C, and a light receiving element. The light receiving element is, for example, a sensor, such as an infrared sensor for detecting light in a near-infrared wavelength range. Preferably, the electronic device is any of an information recognition device, a sorting device, a detection device, or an inspection device. As described above, these devices also facilitate miniaturization of the sensing system and broadening of the sensing range.

The information recognition device is, for example, a driver support system that recognizes the surrounding situation by detecting reflected components of emitted infrared rays.

The sorting device is, for example, a device that sorts an irradiated object into predetermined categories by using the difference in infrared light components between the irradiation light and reflected light reflected by the irradiated object.

The detection device is, for example, a device that detects a liquid. Examples of liquids include water, and flammable liquids that are prohibited from being transported in aircraft. Specifically, the detection device may be a device for detecting moisture adhering to glass, and moisture absorbed by an object, such as sponge or fine powder. The detection device may visualize the detected liquid. Specifically, the detection device may visualize the distribution information of the detected liquid.

The inspection device may be any of a medical inspection device, an agricultural and livestock industry inspection device, a fishery inspection device, or an industrial inspection device. These devices are useful for inspecting an inspection target in each industry.

The medical inspection device is, for example, an examination device that examines the health condition of a human or non-human animal. Non-human animals are, for example, domestic animals. The medical inspection device is, for example, a device used for a biological examination, such as a fundus examination or a blood oxygen saturation examination, and a device used for examination of an organ, such as a blood vessel or an organ. The medical inspection device may be a device for examining the inside of a living body or a device for examining the outside of a living body.

The agricultural and livestock industry inspection device is, for example, a device for inspecting agricultural and livestock products including agricultural products and livestock products. Agricultural products may be used as foods, for example, fruits and vegetables, or cereals, or as fuels, such as oils. Livestock products include, for example, meat and dairy products. The agricultural and livestock industry inspection device may be a device for non-destructively inspecting the inside or outside of the agricultural and livestock products. Examples of the agricultural and livestock industry inspection device includes a device for inspecting the sugar content of vegetables and fruits, a device for inspecting the acidity of vegetables and fruits, a device for inspecting the freshness of vegetables and fruits by the visualization of leaf veins, a device for inspecting the quality of vegetables and fruits by the visualization of wounds and internal defects, a device for inspecting the quality of meat, and a device for inspecting the quality of processed foods processed with milk, meat, or the like as raw materials.

The fishery inspection device is, for example, a device for inspecting the flesh quality of fish, such as tuna, or a device for inspecting the presence or absence of the contents in shells of shellfish.

The industrial inspection device is, for example, a foreign matter inspection device, a content inspection device, a condition inspection device, or a structure inspection device.

Examples of the foreign matter inspection device include a device for inspecting foreign matter in a liquid contained in a container, such as a beverage or a liquid medicine, a device for inspecting foreign matter in a packaging material, a device for inspecting foreign matter in a printed image, a device for inspecting foreign matter in a semiconductor or an electronic component, a device for inspecting foreign matter, such as residual bone in food, dust, or machine oil, a device for inspecting foreign matter in processed food in a container, and a device for inspecting foreign matter in medical devices, such as adhesive plasters, medical and pharmaceutical products, or quasi-drugs.

Examples of the content inspection device include a device for inspecting the content of a liquid contained in a container, such as a beverage or a liquid medicine, a device for inspecting the content of a processed food contained in a container, and a device for inspecting the content of asbestos in building materials.

Examples of the condition inspection device include a device for inspecting packaging state of a packaging material, and a device for inspecting printing state of a packaging material.

Examples of the structure inspection device include an internal non-destructive inspection device and an external non-destructive inspection device for a composite member or a composite component, such as a resin product. A specific example of the resin product is, for example, a metal brush with a part of metal wire embedded in the resin, and the inspection device inspects the bonding state of the resin and the metal.

The electronic device according to the present embodiment may use color night vision technology. The color night vision technology uses a correlation of reflection intensity between visible light and infrared rays to colorize an image by assigning infrared rays to RGB signals for each wavelength. According to the color night vision technology, a color image is obtained only by infrared rays, and it is particularly suitable for a security device.

As described above, the electronic device includes the light emitting device 1, 1A, 1B, 1C. When the light emitting device 1, 1A, 1B, 1C includes the power source, the light source 2, and the wavelength converter 3, 3A, it is not necessary to accommodate all of them in one housing. Thus, the electronic device according to the present embodiment also provides a highly accurate and compact inspection method, or the like, with excellent operability.

[Inspection Method]

Next, an inspection method according to the present embodiment is described. As described above, the electronic device including the light emitting device 1, 1A, 1B, 1C is also usable as an inspection device. That is, the light emitting device 1, 1A, 1B, 1C is usable in the inspection method according to the present embodiment. This provides a highly accurate and compact inspection method with excellent operability.

[Medical Device]

Next, a medical device according to the present embodiment is described. Specifically, as an example of the medical device, an endoscope provided with the light emitting device, and an endoscope system using the endoscope are described.

Figure 9:
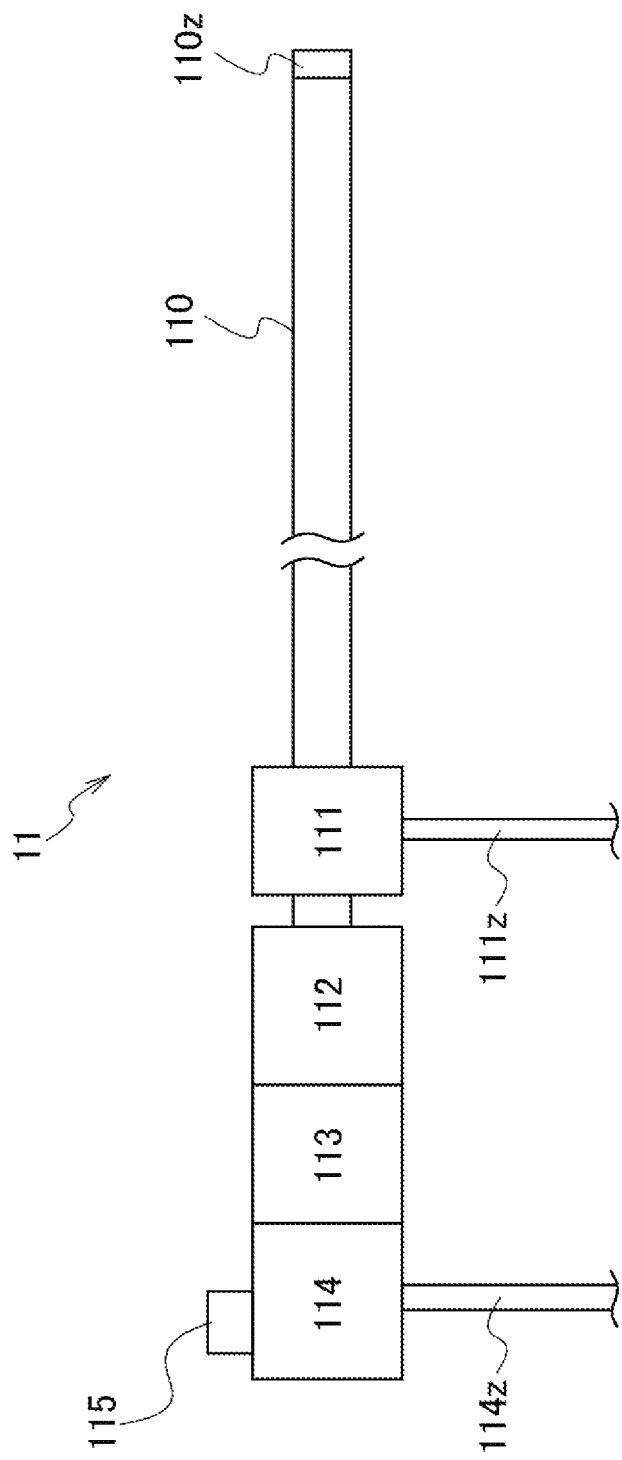
FIG. 9 is a schematic diagram illustrating a configuration of an endoscope according to the present embodiment.

The endoscope according to the present embodiment includes the above-described light emitting device 1, 1A, 1B, 1C. As illustrated in FIG. 9, an endoscope 11 includes a scope 110, a light source connector 111, amount adapter 112, a relay lens 113, a camera head 114, and an operation switch 115.

The scope 110 is an elongated light guide member capable of guiding light from end to end and is inserted into the body when in use. The scope 110 includes an imaging window 110z at its tip. For the imaging window 110z, an optical material, such as optical glass or optical plastics, is used. The scope 110 further includes an optical fiber for guiding light introduced from the light source connector 111 to the tip, and an optical fiber for transmitting an optical image input from the imaging window 110z.

The mount adapter 112 is a member for mounting the scope 110 to the camera head 114. Various scopes 110 are detachably mountable on the mount adapter 112.

The light source connector 111 introduces illumination light emitted by the light emitting device to a diseased part or the like in the body. In the present embodiment, the illumination light includes visible light and near-infrared light. The light introduced into the light source connector 111 is guided to the tip of the scope 110 through the optical fiber and is emitted to a diseased part or the like in the body from the imaging window 110z. As illustrated in FIG. 9, a transmission cable 111z that guides illumination light from the light emitting device to the scope 110 is connected to the light source connector 111. The transmission cable 111z may include an optical fiber.

The relay lens 113 converges the optical image transmitted through the scope 110 on an imaging surface of an image sensor. Note that the relay lens 113 may be moved in accordance with the operation amount of the operation switch 115 to perform focus adjustment and magnification adjustment.

The camera head 114 includes a color separation prism inside. The color separation prism separates, for example, the light converged by the relay lens 113 into R light (red light), G light (green light), and B light (blue light). Note that the color separation prism may further separate an IR light (near-infrared light). This also makes the endoscope 11 capable of identifying a lesion part using the fluorescence imaging method using near-infrared light.

The camera head 114 further includes image sensors as detectors inside. The image sensors each convert an optical image formed on each imaging surface into an electric signal. The image sensors are not limited, but at least one of CCD (Charge Coupled Device) or CMOS (Complementary Metal Oxide Semiconductor) is usable. The image sensors are dedicated sensors for each receiving B component (blue component), R component (red component), or G component (green component) light, for example. Note that the camera head 114 may further include a dedicated sensor for receiving an IR component (near-infrared component). This also makes the endoscope 11 capable of identifying a lesion part using the fluorescence imaging method using near-infrared light.

The camera head 114 may have a color filter inside instead of the color separation prism. The color filter is provided on the imaging surface of the image sensor. For example, three color filters are provided, and the three color filters receive the light converged by the relay lens 113 and selectively transmit R light (red light), G light (green light), and B light (blue light), respectively. Note that the color filter for selectively transmitting an IR light (near-infrared light) is further provided, which makes the endoscope 11 also capable of specifying a lesion part using the fluorescence imaging method using near-infrared light.

When the fluorescence imaging method using near-infrared light is used, preferably, the color filter for selectively transmitting IR light includes a barrier film for cutting the reflection component of near-infrared light (IR light) included in the lighting. This enables only the fluorescence composed of IR light emitted by a fluorescent drug used in the fluorescence imaging method to form an image on the imaging surface of an image sensor for IR light. Therefore, the diseased part luminous with the fluorescent drug is easily observed clearly.

As illustrated in FIG. 9, a signal cable 114z is connected to the camera head 114 to transmit an electric signal from an image sensor to a CCU 12 described later.

In the endoscope 11 having such a configuration, light from a subject is guided to the relay lens 113 through the scope 110 and is further transmitted through the color separation prism in the camera head 114 to form images on the image sensors.

Figure 10:
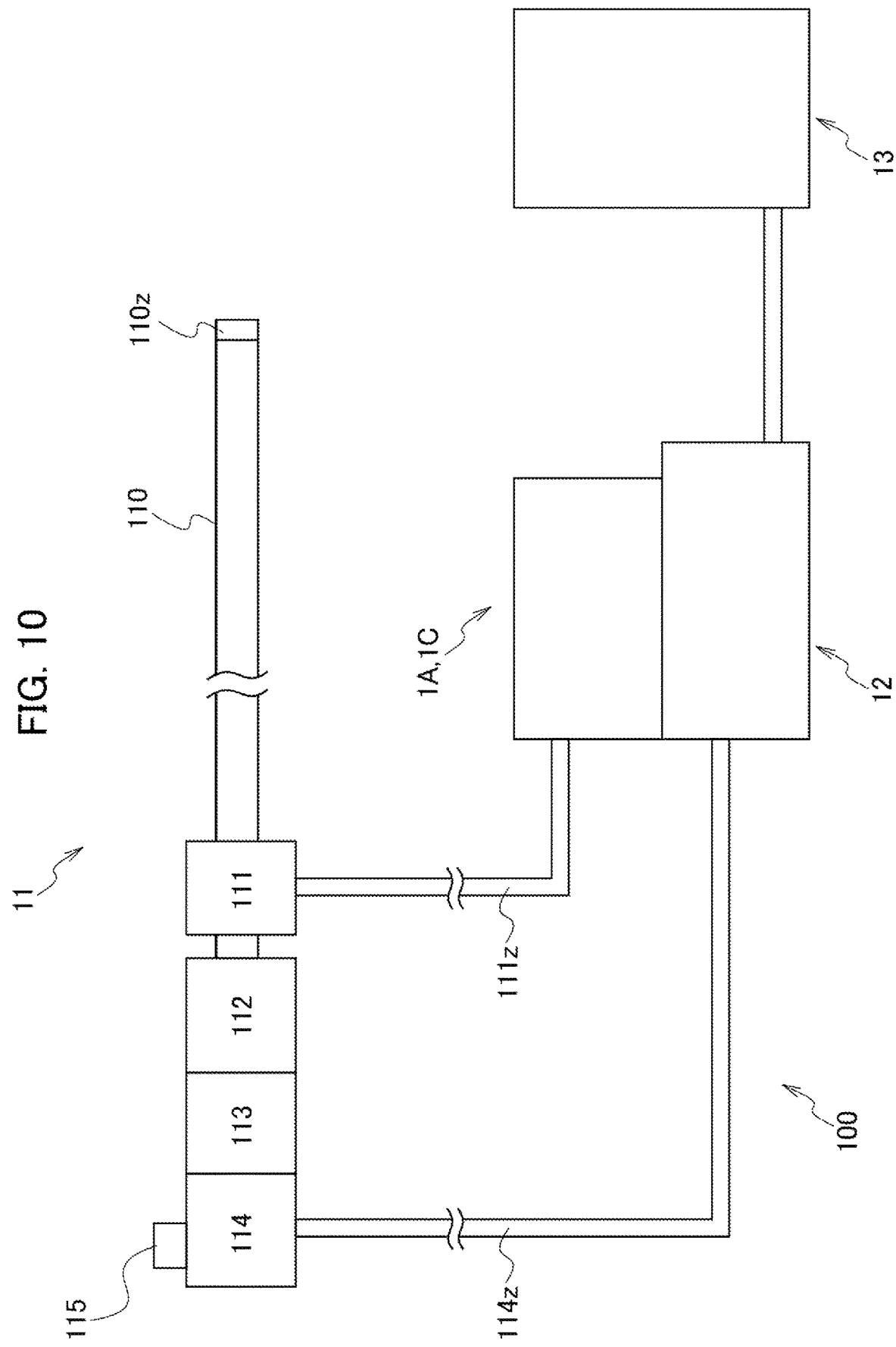
FIG. 10 is a schematic diagram illustrating a configuration of an endoscope system according to the present embodiment.

As illustrated in FIG. 10, the endoscope system 100 according to the present embodiment includes the endoscope 11 for imaging the inside of a subject, the CCU (Camera Control Unit) 12, the light emitting device 1, 1A, 1B, 1C, and a display device 13, such as a display.

The CCU 12 includes at least an RGB signal processing unit, an IR signal processing unit, and an output unit. The CCU 12 executes a program stored in the internal or external memory of the CCU 12 to implement the respective functions of the RGB signal processing unit, the IR signal processing unit, and the output unit.

The RGB signal processing unit converts the electrical signals of the B component, the R component, and the G component from the image sensors into video signals that are displayable on the display device 13 and outputs the video signals to the output unit. The IR signal processing unit converts the electrical signal of the IR component from the image sensor into a video signal and outputs the video signal to the output unit.

The output unit outputs at least one of the video signals of respective RGB color components or the video signal of the IR component to the display device 13. For example, the output unit outputs video signals on the basis of either a simultaneous output mode or a superimposed output mode.

In the simultaneous output mode, the output unit simultaneously outputs the RGB image and the IR image on separate screens. The simultaneous output mode enables the diseased part to be observed by comparing the RGB image and the IR image on the separate screens. In the superimposed output mode, the output unit outputs a composite image in which the RGB image and the IR image are superimposed. The superimposed output mode enables the diseased part luminous with the fluorescent drug used in the fluorescence imaging method to be clearly observed in the RGB image, for example.

The display device 13 displays an image of a target, such as a diseased part, on a screen on the basis of video signals from the CCU 12. In the simultaneous output mode, the display device 13 divides the screen into multiple screens and displays the RGB image and the IR image side by side on each screen. In the superimposed output mode, the display device 13 displays a composite image in which an RGB image and an IR image are superimposed on each other on a single screen.

As described above, the endoscope 11 according to the present embodiment includes the light emitting device 1, 1A, 1B, 1C and emits the first wavelength-converted light 7 through the imaging window 110z of the scope 110. Thus, by using the endoscope 11, it is possible to efficiently excite the fluorescent drug and the photosensitive drug taken into the living body and to make the fluorescent drug and the photosensitive drug function sufficiently.

When the endoscope 11 is provided with the light emitting device 1A, 1C including the second phosphor 8, the endoscope 11 emits the second wavelength-converted light 9 that is visible light in addition to the first wavelength-converted light 7. Thus, by using the endoscope system 100, it is possible to irradiate the diseased part with the first wavelength-converted light 7 while specifying the position of the diseased part.

Preferably, the endoscope 11 according to the present embodiment further includes a detector for detecting fluorescence emitted by a fluorescent drug that has absorbed the first wavelength-converted light 7. By providing the endoscope 11 with the detector for detecting fluorescence emitted by a fluorescent drug in addition to the light emitting device 1, 1A, 1B, 1C, the diseased part is specified only by the endoscope. This makes it possible to perform medical examination and treatment with less burden on the patient, since there is no need to open the abdomen wide to identify the diseased part as in the conventional method. This also enables the doctor using the endoscope 11 to accurately identify the diseased part, which improves the efficiency of treatment.

Preferably, the medical device according to the present embodiment is used for either the fluorescence imaging method or the photodynamic therapy. This medical device illuminates the inside of the living body with a broad near-infrared high output light and makes the fluorescent drug or photosensitive drug taken into the living body fully functional, which is expected to have a large therapeutic effect. Such a medical device uses the light emitting device 1, 1A, 1B, 1C having a relatively simple configuration, which is advantageous in reducing the size and the cost.

Example 1

Next, the light emitting device according to the present embodiment is described in more detail with reference to example 1, but the present embodiment is not limited thereto.

[Preparation of Phosphor]

Example 1-1

The oxide phosphor used in example 1-1 was synthesized using a preparation method utilizing a solid phase reaction. The phosphor of example 1-1 is an oxide phosphor represented by a composition formula of $(Al_{0.99}, Cr_{0.01})_2O_3$. The phosphor of example 1-1 is a $Cr^{3+}$-activated phosphor.

In synthesizing the oxide phosphor of example 1-1, the following compound powders were used as main raw materials.

Aluminum hydroxide oxide (AlOOH): purity 2N5, manufactured by KAWAI LIME INDUSTRY CO., LTD.

Chromium oxide ($Cr_2O_3$): purity 3N, manufactured by Kojundo Chemical Laboratory Co., Ltd.

First, the above-described raw materials were weighed to obtain a compound of a stoichiometric composition $(Al_{0.99}, Cr_{0.01})_2O_3$. The weighed raw materials were then put into a beaker containing pure water and stirred with a magnetic stirrer for 1 hour. Thus, a slurry-like mixed raw material of the pure water and raw materials was obtained. Then, the slurry-like mixed raw material was dried entirely using a dryer. The mixed raw material after drying was pulverized using a mortar and a pestle to obtain a raw material for calcining.

Next, the above-described raw material for calcining was transferred to a small alumina crucible and calcined in air at 1500° C. for 4 hours in a box-type electric furnace. Note that the temperature rise and fall rate during calcining was set at 400° C./h. As a result, the phosphor of example 1-1 represented by the composition formula of $(Al_{0.99}, Cr_{0.01})_2O_3$ was obtained.

Example 1-2

The oxide phosphor used in example 1-2 was synthesized using a preparation method utilizing a solid phase reaction. The phosphor of example 1-2 is an oxide phosphor represented by a composition formula of $Gd_3(Ga_{0.97}, Cr_{0.03})_5O_{12}$. The phosphor of example 1-2 is a $Cr^{3+}$-activated phosphor.

In synthesizing the oxide phosphor of example 1-2, the following compound powders were used as main raw materials.

Gadolinium oxide ($Gd_2O_3$): purity 3N, Wako Pure Chemical Corporation

Gallium oxide ($Ga_2O_3$): purity 4N, Wako Pure Chemical Corporation

Chromium oxide ($Cr_2O_3$): purity 3N, Kojundo Chemical Laboratory Co., Ltd.

First, the above-described raw materials were weighed to obtain a compound of a stoichiometric composition $Gd_3(Ga_{0.97}, Cr_{0.03})_5O_{12}$. The weighed raw materials were then put into a beaker containing pure water and stirred with a magnetic stirrer for 1 hour. Thus, a slurry-like mixed raw material of the pure water and raw materials was obtained. Then, the slurry-like mixed raw material was dried entirely using a dryer. The mixed raw material after drying was pulverized using a mortar and a pestle to obtain a raw material for calcining.

Next, the above-described raw material for calcining was transferred to a small alumina crucible and calcined in air at 1500° C. for 4 hours in a box-type electric furnace. Note that the temperature rise and fall rate during calcining was set at 400° C./h. As a result, the phosphor of example 1-2 represented by the composition formula of $Gd_3(Ga_{0.97}, Cr_{0.03})_5O_{12}$ was obtained.

Example 1-3

The oxide phosphor used in example 1-3 was synthesized using a preparation method utilizing a solid phase reaction. The phosphor of example 1-3 is an oxide phosphor represented by a composition formula of $(Ga_{0.99}, Cr_{0.01})_2O_3$. The phosphor of example 1-3 is a $Cr^{3+}$-activated phosphor.

In synthesizing the oxide phosphor of example 1-3, the following compound powders were used as main raw materials.

Gallium oxide ($Ga_2O_3$): purity 4N, Wako Pure Chemical Corporation

Chromium oxide ($Cr_2O_3$): purity 3N, Kojundo Chemical Laboratory Co., Ltd.

First, the above-described raw materials were weighed to obtain a compound of a stoichiometric composition $(Ga_{0.99}, Cr_{0.01})_2O_3$. The weighed raw materials were then put into a beaker containing pure water and stirred with a magnetic stirrer for 1 hour. Thus, a slurry-like mixed raw material of the pure water and raw materials was obtained. Then, the slurry-like mixed raw material was dried entirely using a dryer. The mixed raw material after drying was pulverized using a mortar and a pestle to obtain a raw material for calcining.

Next, the above-described raw material for calcining was transferred to a small alumina crucible and calcined in air at 1500° C. for 4 hours in a box-type electric furnace. Note that the temperature rise and fall rate during calcining was set to 400° C./h. As a result, the phosphor of example 1-3 represented by the composition formula of $(Ga_{0.99}, Cr_{0.01})_2O_3$ was obtained.

(Reference Example 1-1)

As the oxide phosphor of reference example 1-1, a phosphor represented by a composition formula of $(Y, Ce)_3Al_5O_{12}$ was used. The phosphor of reference example 1-1 is a $Ce^{3+}$*-activated phosphor. Note that the phosphor used has product number Y996, manufactured by Nemoto & Co., Ltd.

(Reference Example 1-2)

As the oxide phosphor of reference example 1-2, a phosphor represented by a composition formula of $(Sr, Ca, Eu)AlSiN_3$ was used. The phosphor of reference example 1-2 is an $Eu^{2+}$-activated phosphor. Note that the phosphor used has product number BR-102C, manufactured by Mitsubishi Chemical Corporation.

[Evaluation]

(Luminescence Lifetime Measurement)

The luminescence lifetime (1/e decay time) of the phosphors of examples 1-1 to 1-3 and reference examples 1-1 to 1-2 was measured by a luminescence lifetime measuring device (Quantaurus-Tau compact luminescence lifetime measuring device manufactured by Hamamatsu Photonics K.K.) The measurement results of the luminescence lifetime are illustrated in table 3 and FIG. 11.

TABLE 3

| | Composition formula | Abbreviation | 1/e decay time (μs) |
|---|---|---|---|
| Example 1-1 | $(Al_{0.99}, Cr_{0.01})_2O_3$ | $Al_2O_3:Cr^{3+}$ | 1895 |
| Example 1-2 | $Gd_3(Ga_{0.97}, Cr_{0.03})_5O_{12}$ | $GGG:Cr^{3+}$ | 104 |
| Example 1-3 | $(Ga_{0.99}, Cr_{0.01})_2O_3$ | $Ga_2O_3:Cr^{3+}$ | 77 |
| Reference example 1-1 | $(Y, Ce)_3Al_5O_{12}$ | $YAG:Ce^{3+}$ | 0.06 |
| Reference example 1-2 | $(Sr, Ca, Eu)AlSiN_3$ | $S-CASN:Eu^{2+}$ | 0.676 |

Figure 11:
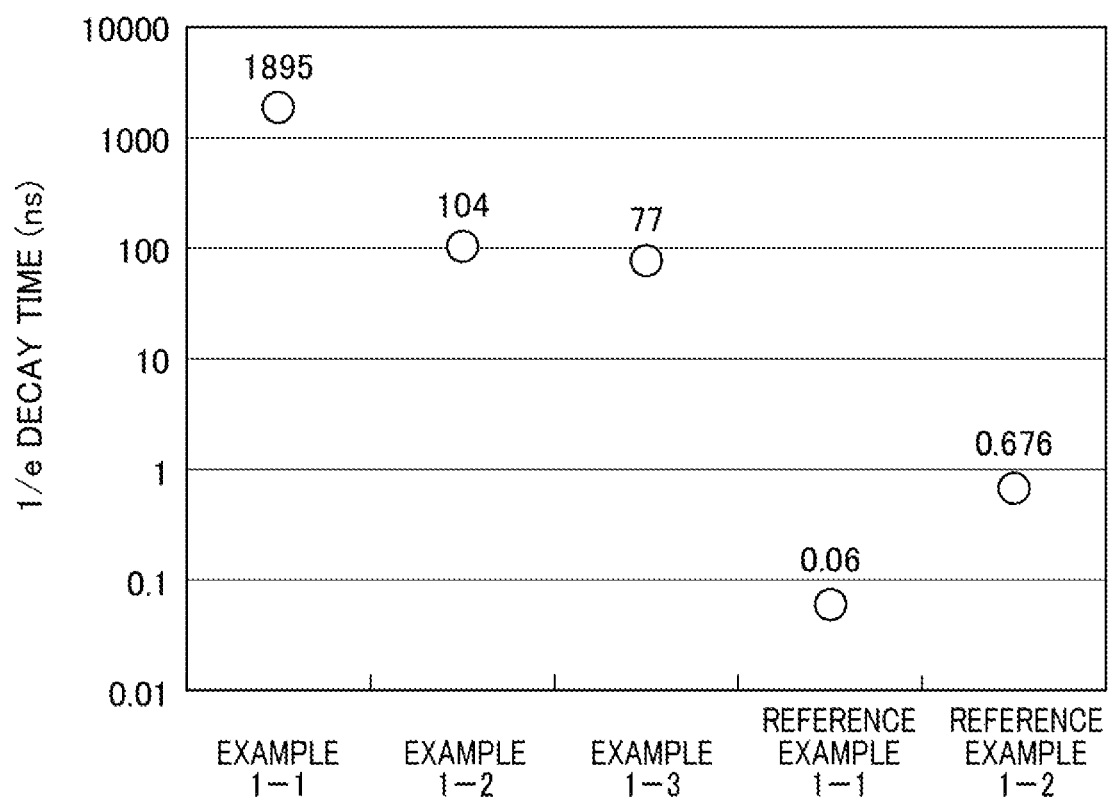
FIG. 11 is a graph illustrating a luminescence lifetime (1/e decay time) of phosphors of examples 1-1 to 1-3 and reference examples 1-1 to 1-2.

As illustrated in table 3 and FIG. 11, the phosphors of examples 1-1 to 1-3 each have a luminescence lifetime (1/e decay time) of 77 μs or more, which is 100 times longer than that of the $Ce^{3+}$-activated phosphor of reference example 1-1 and that of the $Eu^{2+}$-activated phosphor of reference example 1-2.

(Spectroscopic Property)

Next, the fluorescence spectra of the phosphors of examples 1-1 to 1-3 were measured using a quantum yield measuring device (absolute PL quantum yield spectrometer C9920-02, manufactured by Hamamatsu Photonics K.K.) to determine the fluorescence peak wavelength. Note that the excitation wavelength at the time of fluorescence spectrum measurement was set to 450 nm (E1=2.76 eV). Table 4 illustrates the fluorescence peak wavelength of each phosphor of examples 1-1 to 1-3 and the energy conversion value (E2) at the fluorescence peak wavelength. Table 4 further illustrates the sum (E1+E2) of the energy conversion value (E1) of the excitation light having a peak wavelength of 450 nm and the energy conversion value (E2) at the fluorescence peak wavelength in each phosphor of examples 1-1 to 1-3. Table 4 also illustrates the bandgap energy (Eg) of the host crystal constituting each phosphor of examples 1-1 to 1-3.

TABLE 4

| | Abbreviation | Fluorescence peak wavelength (nm) | Energy conversion value at fluorescence peak wavelength (E2) (eV) | E1 + E2 (eV) | Bandgap (Eg) (eV) |
|---|---|---|---|---|---|
| Example 1-1 | $Al_2O_3:Cr^{3+}$ | 694 | 1.79 | 4.55 | 8.8 |
| Example 1-2 | $GGG:Cr^{3+}$ | 730 | 1.70 | 4.46 | 6.4 |
| Example 1-3 | $Ga_2O_3:Cr^{3+}$ | 712 | 1.74 | 4.50 | 4.8 |
| Reference example 1-1 | $YAG:Ce^{3+}$ | — | — | — | — |
| Reference example 1-2 | $S-CASN:Eu^{2+}$ | — | — | — | — |

(Fluorescence Output Saturation Property)

Next, wavelength conversion devices were made respectively using the phosphors of examples 1-1 to 1-3 and reference examples 1-1 to 1-2, and the fluorescence output saturation property of the phosphors was evaluated. Specifically, a phosphor paste was prepared by mixing the phosphor powder of each example and each reference example and a sealing material using a mortar and pestle so that the filling ratio of the phosphor was 40 vol %. Note that the sealing material used was polysilsesquioxane ($RSiO_{1.5}$), grade SR-13, manufactured by Konishi Chemical Ind. Co., Ltd.

Next, as illustrated in FIG. 12, a sapphire substrate 203 (length 9 mm, width 9 mm, thickness 0.5 mm) having a dichroic mirror 201 on one side and an anti-reflection coating (AR coating) 202 on the other side was prepared. Then, the above-described phosphor paste was applied to the surface of the dichroic mirror 201 of the sapphire substrate by a screen printing method. The mesh printing plate used for screen printing was a circular plate having a mesh opening of 74 μm (200 mesh) and a diameter of 7.8 mm. Thereafter, the sapphire substrate 203 applied with the phosphor paste was subjected to a heat treatment at 200° C. for 2 hours to harden the sealing material, thereby obtaining a wavelength conversion device 200 provided with a phosphor layer 204 including each phosphor of examples and reference examples.

Figure 13:
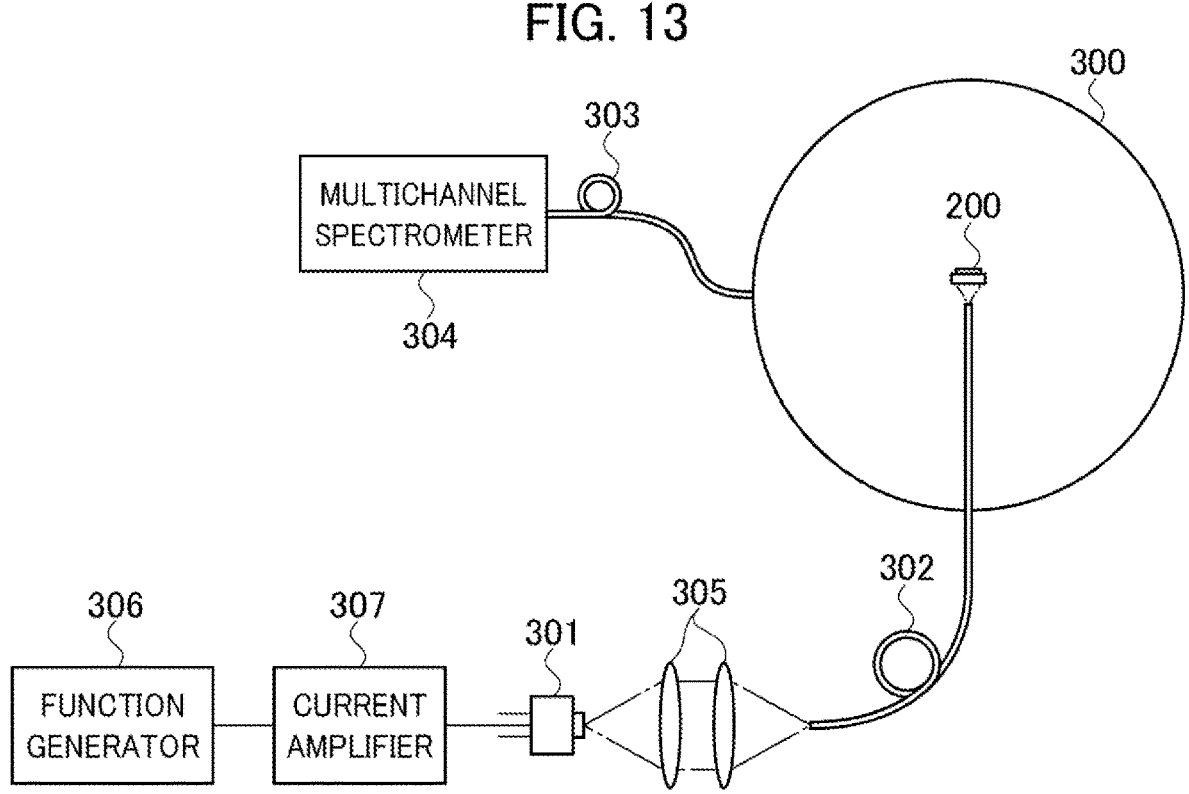
FIG. 13 is a schematic diagram illustrating a device for measuring a luminescence intensity of each phosphor of examples 1-1 to 1-3 and reference examples 1-1 to 1-2 in example 1.

Next, the luminescence intensity of each phosphor was measured using an evaluation device illustrated in FIG. 13. Specifically, first, each wavelength conversion device 200 according to examples and reference examples obtained as described above was placed at the center of an integrating sphere 300. Next, a blue laser beam (peak wavelength: 450 nm) emitted by a blue laser diode element 301 installed outside the integrating sphere 300 was guided to the center of the integrating sphere 300 by using an optical fiber 302 to be emitted to the wavelength conversion device 200. The luminescence property of the fluorescence emitted by the wavelength conversion device 200 was measured by a multichannel spectrometer 304 connected to the integrating sphere 300 via an optical fiber 303. As illustrated in FIG. 13, a collimator lens 305 is interposed between the blue laser diode element 301 and a light input end of the optical fiber 302.

Figure 14:
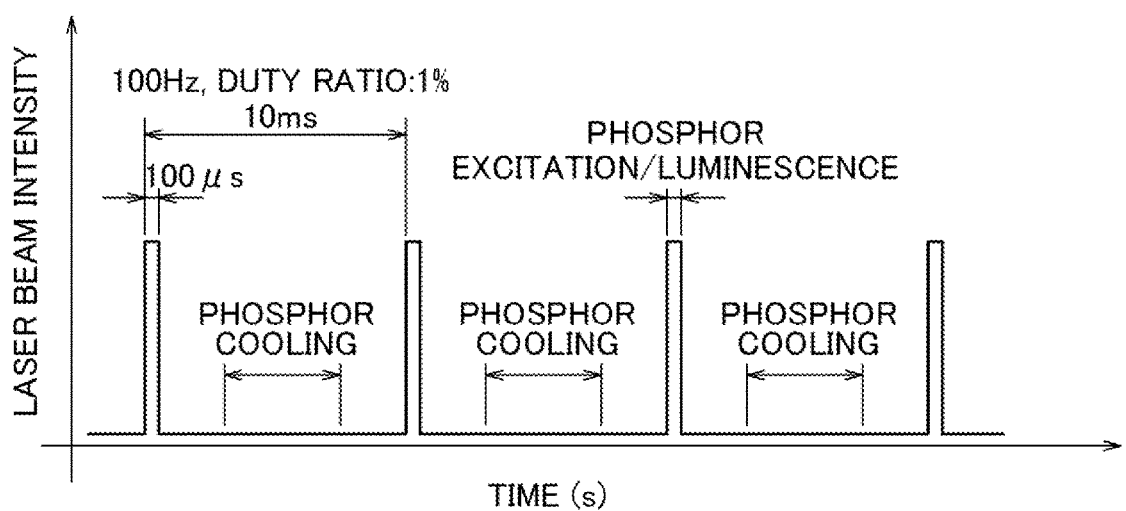
FIG. 14 is a graph illustrating a duty ratio of a blue laser beam used in evaluation of the fluorescence output saturation property in example 1.

In general, the blue laser diode element is CW driven (Continuous Wave). Thus, as the power density of the excitation light increases, the amount of heat generated by the phosphor increases, and the thermal quenching of the phosphor occurs. Then, for the purpose of separating the thermal quenching of the phosphor and the light output saturation, a function generator 306 and a current amplifier 307 were used to convert the blue laser beam emitted by the blue laser diode element 301 into a pulsed light having a frequency of 100 Hz and a duty ratio of 1%. That is, as illustrated in FIG. 14, in a cycle of 10 ms, the time for irradiating the phosphor with the blue laser beam was set to 100 μs, and the remaining time was set to the cooling time of the phosphor.

Then, the irradiation area of the wavelength conversion device 200 with the blue laser beam was set to 0.6 mmφ, and the rated output of the blue laser beam was changed from 0.16 W/mm$^2$ to 4.00 W/mm$^2$, thereby evaluating the saturation of the fluorescence output of each phosphor of examples and reference examples.

Figure 15:
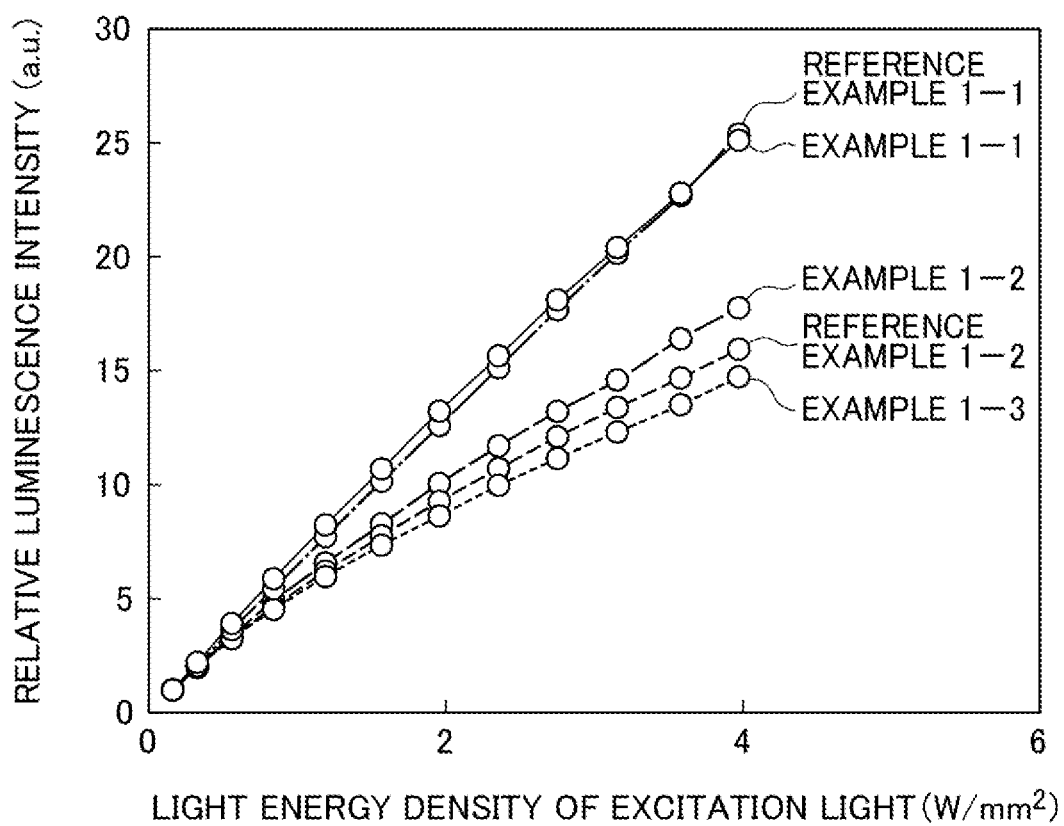
FIG. 15 is a graph illustrating a relationship between a relative luminescence intensity and a light energy density of an excitation light in the phosphors of examples 1-1 to 1-3 and reference examples 1-1 to 1-2.

FIG. 15 illustrates the relative intensity of fluorescence emitted by each phosphor when the energy of the laser beam is changed from 0.16 W/mm$^2$ to 4.00 W/mm$^2$. As illustrated in FIG. 15, the phosphors of examples 1-1 to 1-3 and reference examples 1-1 to 1-2 emitted high energy fluorescence even when the energy density of the laser light was increased from 0.16 W/mm$^2$ to 4.00 W/mm$^2$. That is, it is understood that not only the phosphors of reference examples 1-1 to 1-2 having a short luminescence lifetime, but also the phosphors of examples 1-1 to 1-3 having a long luminescence lifetime do not have saturation of fluorescence output and emit fluorescence of high energy.

As illustrated in table 4, the sum of E1 and E2 in each phosphor of examples 1-1 to 1-3 is smaller than the bandgap energy Eg of the host crystal. Therefore, it is found that appropriately adjusting the wavelength of the excitation light, and the bandgap energy and the luminescence wavelength of the phosphor reduces the generation of the excited state absorption (ESA) and prevents the fluorescence output saturation even when the high energy laser light is used as the excitation light.

Example 2

Next, the phosphor represented by the above general formula (I) that is usable in the light emitting device according to the present embodiment is described in more detail with reference to example 2, but the present embodiment is not limited thereto.
[Preparation of Phosphor]
(Reference Example 2-1)

The oxide phosphor used in reference example 2-1 was synthesized using a preparation method utilizing a solid phase reaction. The phosphor of reference example 2-1 is an oxide phosphor represented by a composition formula of $(Gd_{0.75}La_{0.25})_3(Ga_{0.97}Cr_{0.03})_2Ga_3O_{12}$. The phosphor of reference example 2-1 is a $Cr^{3+}$-activated phosphor.

In synthesizing the oxide phosphor of reference example 2-1, the following compound powders were used as main raw materials.

Gadolinium oxide ($Gd_2O_3$): purity 3N, Wako Pure Chemical Corporation

Lanthanum oxide ($La_2O_3$): purity 4N, Wako Pure Chemical Corporation

Gallium oxide ($Ga_2O_3$): purity 4N, Wako Pure Chemical Corporation

Chromium oxide ($Cr_2O_3$): purity 3N, Kojundo Chemical Laboratory Co., Ltd.

First, the above-described raw materials were weighed to obtain a compound of a stoichiometric composition $(Gd_{0.75}La_{0.25})_3(Ga_{0.97}Cr_{0.03})_2Ga_3O_{12}$. The weighed raw material were then put into a beaker containing pure water and stirred with a magnetic stirrer for 1 hour. Thus, a slurry-like mixed raw material of the pure water and raw materials was obtained. Then, the slurry-like mixed raw material was dried entirely using a dryer. The mixed raw material after drying was pulverized using a mortar and a pestle to obtain a raw material for calcining.

Next, the above-described raw material for calcining was transferred to a small alumina crucible and calcined in air at 1450° C. for 1 hour in a box-type electric furnace. Note that the temperature rise and fall rate during calcining was set at 400° C./h. As a result, the phosphor of reference example 2-1 was obtained. The body color of the obtained phosphor was dark green.

Example 2-1

The oxide phosphor used in example 2-1 was synthesized using a preparation method utilizing a solid phase reaction. The phosphor of example 2-1 is an oxide phosphor represented by a composition formula of $(Gd_{0.75}La_{0.25})_3(Ga_{0.90}Sc_{0.07}Cr_{0.03})_2Ga_3O_{12}$. The phosphor of example 2-1 is a $Cr^{3+}$-activated phosphor.

In synthesizing the oxide phosphor of example 2-1, the following compound powders were used as main raw materials.

Gadolinium oxide ($Gd_2O_3$): purity 3N, Wako Pure Chemical Corporation

Lanthanum oxide ($La_2O_3$): purity 4N, Wako Pure Chemical Corporation

Gallium oxide ($Ga_2O_3$): purity 4N, Wako Pure Chemical Corporation

Scandium oxide ($Sc_2O_3$): Purity 4N, Shin-Etsu Chemical Co., Ltd.

Chromium oxide ($Cr_2O_3$): purity 3N, Kojundo Chemical Laboratory Co., Ltd.

First, for the phosphor of example 2-1, the above-described raw materials were weighed to obtain a compound of a stoichiometric composition $(Gd_{0.75}La_{0.25})_3(Ga_{0.90}Sc_{0.07}Cr_{0.03})_2Ga_3O_{12}$. The weighed raw materials were then put into a beaker containing pure water and stirred with a magnetic stirrer for 1 hour. Thus, a slurry-like mixed raw material of the pure water and raw materials was obtained. Then, the slurry-like mixed raw material was dried entirely using a dryer. The mixed raw material after drying was pulverized using a mortar and a pestle to obtain a raw material for calcining.

Next, the above-described raw material for calcining was transferred to a small alumina crucible and calcined in air at 1450° C. for 1 hour in a box-type electric furnace. Note that the temperature rise and fall rate during calcining was set at 400° C./h. As a result, the phosphor of example 2-1 was obtained. The body color of the obtained phosphor was dark green.

Examples 2-2, 2-3, 2-4, and Reference Example 2-2

The oxide phosphors used in examples 2-2, 2-3, 2-4, and reference example 2-2 were synthesized using a preparation method utilizing a solid phase reaction. The phosphors of example 2-2, 2-3, 2-4 are oxide phosphors represented by composition formulae of $(Gd_{0.75}La_{0.25})_3(Ga_{0.75}Sc_{0.22}Cr_{0.03})_2Ga_3O_{12}$, $(Gd_{0.75}La_{0.25})_3(Ga_{0.50}Sc_{0.47}Cr_{0.03})_2Ga_3O_{12}$, $(Gd_{0.75}La_{0.25})_3(Ga_{0.38}Sc_{0.59}Cr_{0.03})_2Ga_3O_{12}$, respectively. The phosphor of reference example 2-2 is an oxide phosphor represented by a composition formula of $(Gd_{0.75}La_{0.25})_3(Ga_{0.25}Sc_{0.72}Cr_{0.03})_2Ga_3O_{12}$. The phosphors of examples 2-2, 2-3, 2-4, and reference example 2-2 are all $Cr^{3+}$-activated phosphors.

2-1 to 2-2, respectively. For reference, FIG. 16 also illustrates the pattern of the garnet compound $Gd_3Ga_2Ga_3O_{12}$ registered in the ICSD (Inorganic Crystal Structure Database). As is seen from FIG. 16, the XRD patterns of the phosphors of examples 2-1 to 2-4 and reference examples 2-1 to 2-2 were approximately consistent with the pattern of $Gd_3Ga_2Ga_3O_{12}$ registered in the ICSD. This indicates that the phosphors of examples 2-1 to 2-4 and reference examples 2-1 to 2-2 are mainly made from a compound having the same garnet crystal structure as $Gd_3Ga_2Ga_3O_{12}$.

From the above results, the phosphors of examples 2-1 to 2-4 and reference examples 2-1 to 2-2 are considered to be compounds represented by the formulas in table 5, respectively. Table 5 also illustrates the concentration of scandium (y-value) in each phosphor.

TABLE 5

| | Composition formula | Scandium concentration (y) (%) | Internal quantum efficiency (%) | Fluorescence peak wavelength (nm) | Relative intensity of ICG excitation spectrum | ICG absorption efficiency relative value |
|---|---|---|---|---|---|---|
| Reference example 2-1 | $(Gd_{0.75}La_{0.25})_3(Ga_{0.97}CR_{0.03})_2Ga_3O_{12}$ | 0 | 80 | 750 | 60 | 48.0 |
| Example 2-1 | $(Gd_{0.75}La_{0.25})_3(Ga_{0.90}Sc_{0.07}Cr_{0.03})_2Ga_3O_{12}$ | 7 | 69 | 759 | 80 | 55.2 |
| Example 2-2 | $(Gd_{0.75}La_{0.25})_3(Ga_{0.75}Sc_{0.22}Cr_{0.03})_2Ga_3O_{12}$ | 22 | 78 | 760 | 80 | 62.4 |
| Example 2-3 | $(Gd_{0.75}La_{0.25})_3(Ga_{0.50}Sc_{0.47}Cr_{0.03})_2Ga_3O_{12}$ | 47 | 76 | 766 | 85 | 64.6 |
| Example 2-4 | $(Gd_{0.75}La_{0.25})_3(Ga_{0.38}Sc_{0.59}Cr_{0.03})_2Ga_3O_{12}$ | 59 | 61 | 770 | 90 | 54.9 |
| Reference example 2-2 | $(Gd_{0.75}La_{0.25})_3(Ga_{0.25}Sc_{0.72}Cr_{0.03})_2Ga_3O_{12}$ | 72 | 46 | 766 | 85 | 39.1 |

First, for the phosphors of examples 2-2, 2-3, and 2-4, the above-described raw materials were weighed to obtain compounds of stoichiometric compositions of $(Gd_{0.75}La_{0.25})_3(Ga_{0.75}Sc_{0.22}Cr_{0.03})_2Ga_3O_{12}$, $(Gd_{0.75}La_{0.25})_3(Ga_{0.50}Sc_{0.47}Cr_{0.03})_2Ga_3O_{12}$, $(Gd_{0.75}La_{0.25})_3(Ga_{0.38}Sc_{0.59}Cr_{0.03})_2Ga_3O_{12}$, respectively. Further, for the phosphor of reference example 2-2, the above-described materials were weighed to obtain a compound of a stoichiometric composition of $(Gd_{0.75}La_{0.25})_3(Ga_{0.25}Sc_{0.72}Cr_{0.03})_2Ga_3O_{12}$. The weighed raw materials were then put into a beaker containing pure water and stirred with a magnetic stirrer for 1 hour. Thus, each slurry-like mixed raw material of the pure water and raw materials was obtained. Then, the slurry-like mixed raw material was dried entirely using a dryer. The mixed raw material after drying was pulverized using a mortar and a pestle to obtain a raw material for calcining.

Next, the above-described raw material for calcining was transferred to a small alumina crucible and calcined in air at 1550° C. for 1 hour in a box-type electric furnace. Note that the temperature rise and fall rate during calcining was set at 400° C./h. As a result, the phosphors of examples 2-2, 2-3, 2-4, and reference example 2-2 were obtained. The body color of all the obtained phosphors was dark green.
[Evaluation]
(Crystal Structure Analysis)

The crystal structures of the phosphors of examples 2-1 to 2-4 and reference examples 2-1 to 2-2 were evaluated using an X-ray diffraction apparatus (benchtop X-ray diffractometer MiniFlex (registered trademark), manufactured by Rigaku Corporation).

Figure 16:
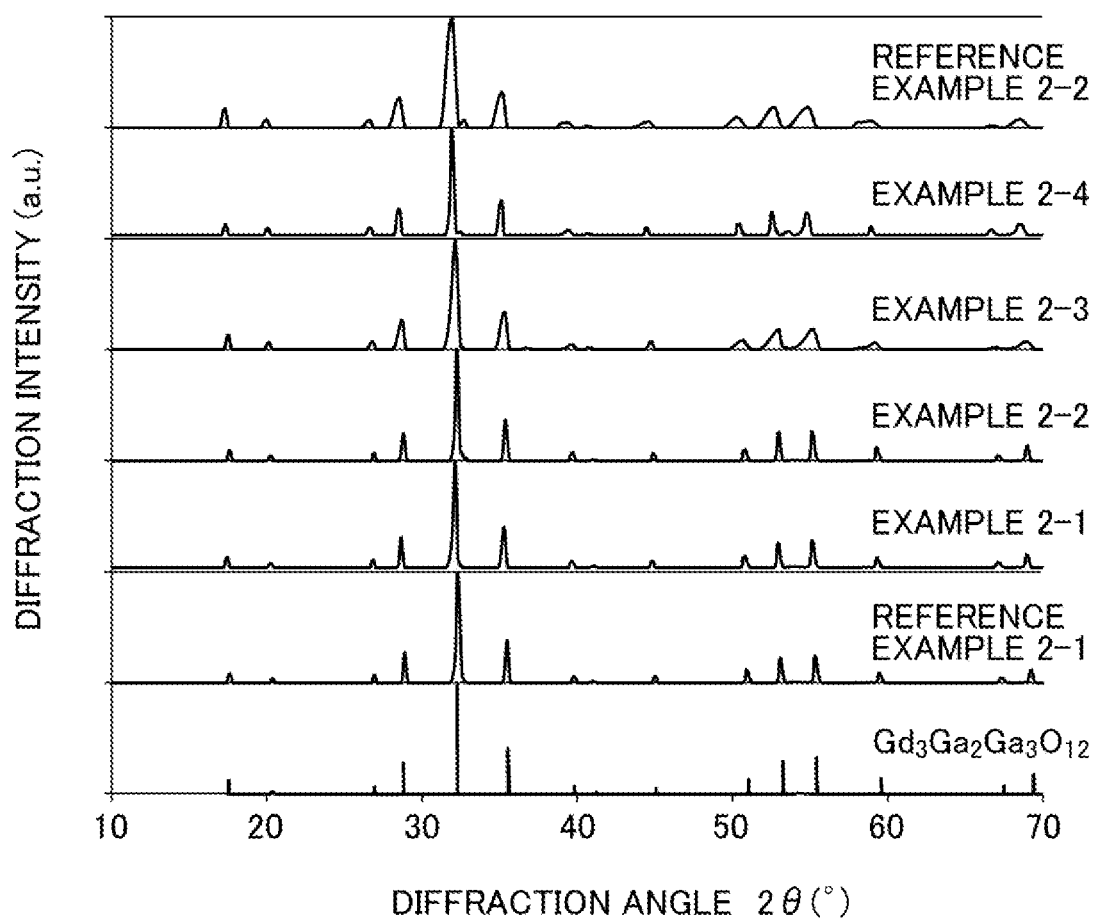
FIG. 16 is a graph illustrating X-ray diffraction patterns of phosphors of examples 2-1 to 2-4 and reference examples 2-1 to 2-2, and that of a garnet compound $Gd_3Ga_2Ga_3O_{12}$ registered in ICSD.

FIG. 16 illustrates X-ray diffraction (XRD) patterns of the phosphors of examples 2-1 to 2-4 and reference examples (Spectroscopic Property)

Figure 17:
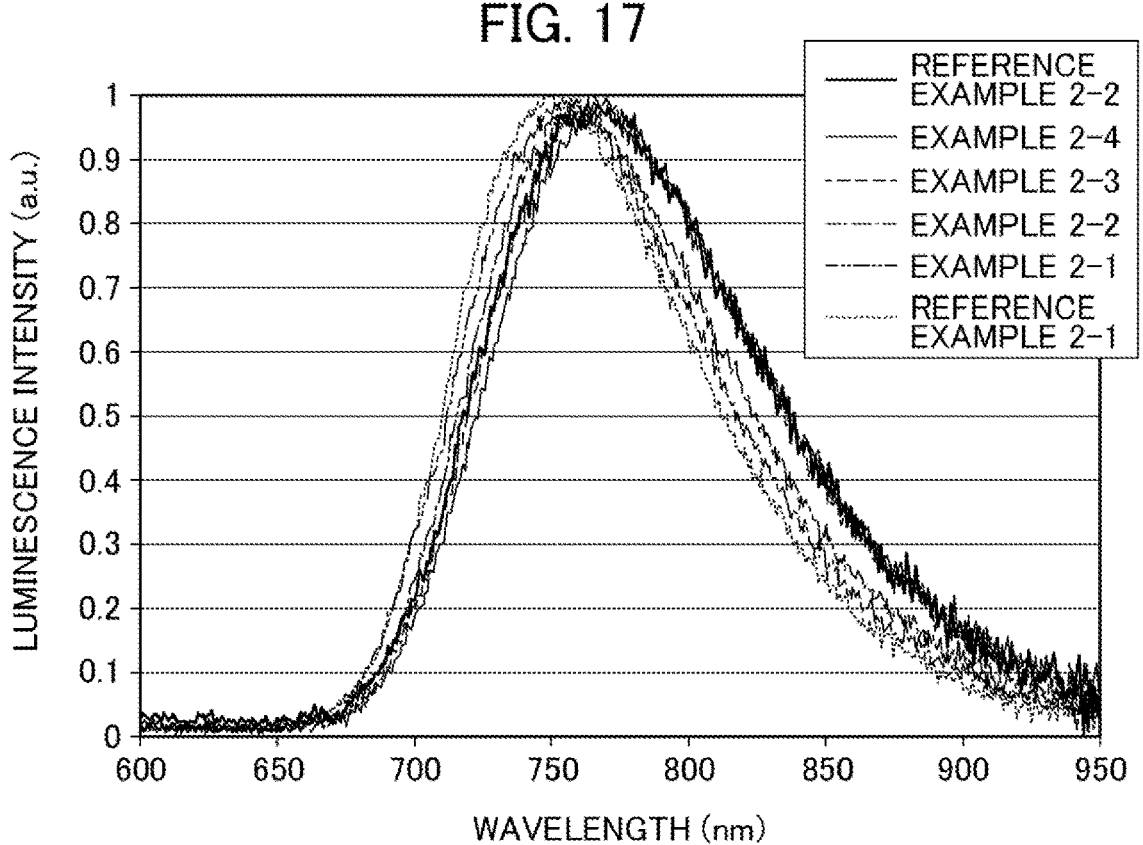
FIG. 17 is a graph illustrating luminescence spectra of the phosphors of examples 2-1 to 2-4 and reference examples 2-1 to 2-2.

Next, the fluorescence spectra and internal quantum efficiencies of the phosphors of examples 2-1 to 2-4 and reference examples 2-1 to 2-2 were evaluated using a quantum yield measuring device (absolute PL quantum yield spectrometer C9920-02, manufactured by Hamamatsu Photonics K.K.) FIG. 17 illustrates the fluorescence spectra of the phosphors of examples 2-1 to 2-4 and reference examples 2-1 to 2-2. Note that the excitation wavelength at the time of fluorescence spectrum measurement was set to 450 nm. In FIG. 17, all the fluorescence spectra are normalized to have the emission peak as 1.

The fluorescence spectra of the phosphors of examples 2-1 to 2-4 and reference examples 2-1 to 2-2 were all broad spectra considered to be attributed to the d-d transition of $Cr^3$. The peak wavelengths of the fluorescence spectra of the phosphors of examples 2-1 to 2-4 were 759 nm, 760 nm, 766 nm, and 770 nm, respectively, as illustrated in table 5. The peak wavelengths of the fluorescence spectra of the phosphors of reference examples 2-1 to 2-2 were 750 nm and 766 nm, respectively. This indicates that the fluorescence spectra of the phosphors of examples 2-1 to 2-4 and reference example 2-2 have a larger overlap with the excitation spectrum (excitation peak wavelength: about 780 nm) of indocyanine green (ICG) than the fluorescence spectrum of the phosphor of reference example 2-1 has.

Note that the internal quantum efficiencies of the phosphors of examples 2-1 to 2-4 were 69%, 78%, 76%, and 61%, respectively, as illustrated in table 5. The internal quantum efficiencies of the phosphors of reference examples 2-1 and 2-2 were 80%, and 46%, respectively.

Figure 18:
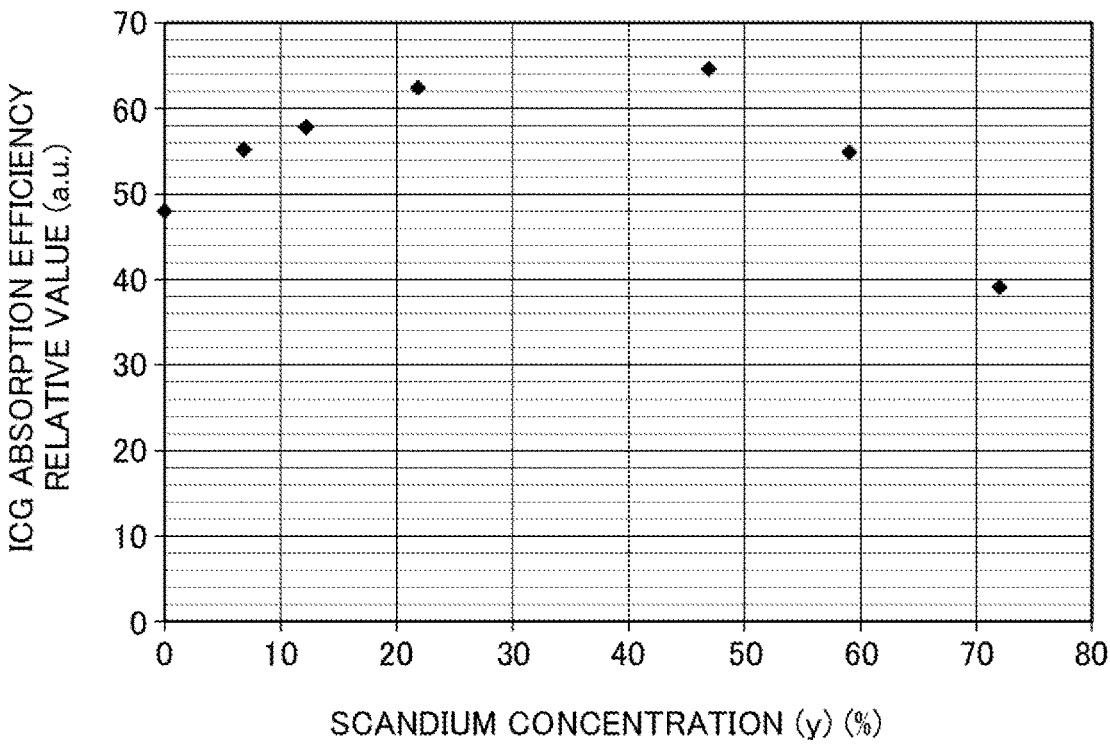
FIG. 18 is a graph illustrating ICG absorption efficiency relative values of the phosphors of examples 2-1 to 2-4 and reference examples 2-1 to 2-2.

Next, the extent to which indocyanine green (ICG), which is a drug for fluorescence imaging, could absorb the fluorescence of the phosphors of examples 2-1 to 2-4 and reference examples 2-1 to 2-2 was calculated. FIG. 18 illustrates ICG absorption efficiency relative values of phosphors of examples 2-1 to 2-4 and reference examples 2-1 to 2-2. Here, the "ICG absorption efficiency relative value" is a value obtained by multiplying the relative value of the intensity of the excitation spectrum of ICG at the fluorescence peak wavelength of each phosphor when the intensity of the excitation spectrum of ICG at the wavelength of 780 nm is 100 by the internal quantum efficiency (%) of each phosphor.

Figure 19:
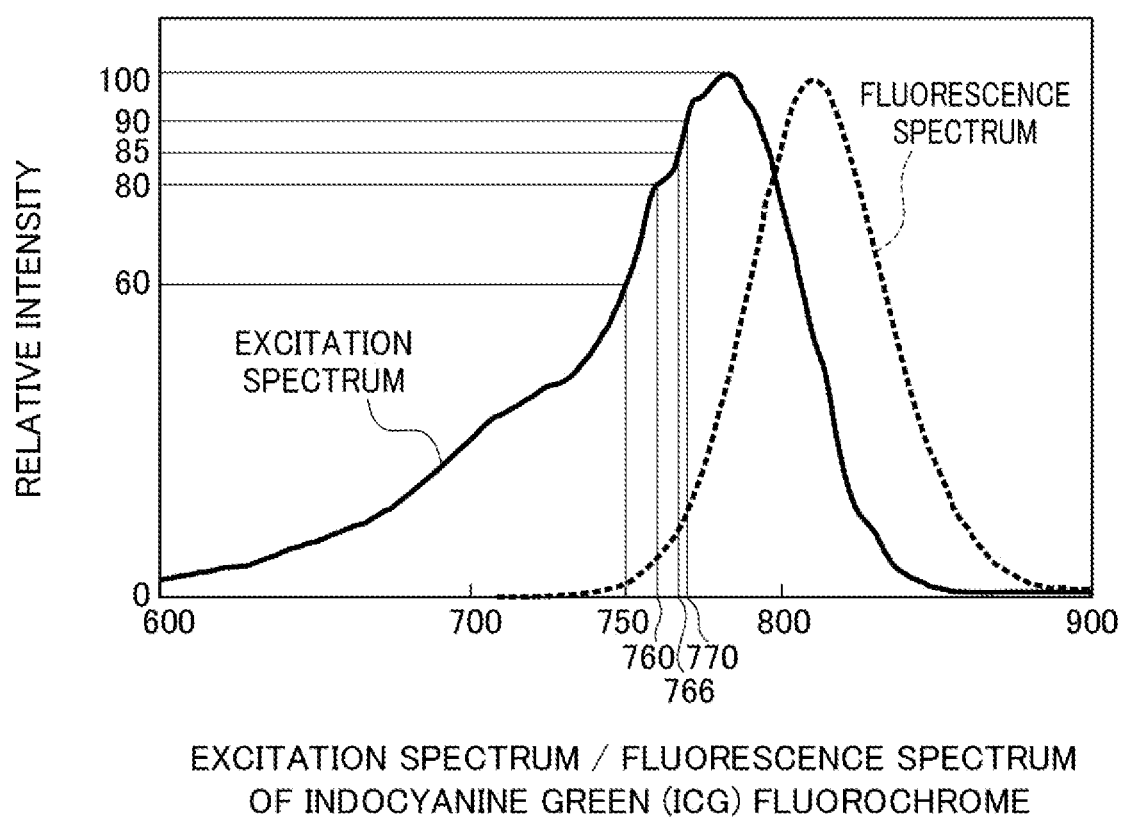
FIG. 19 is a graph illustrating an excitation spectrum and a fluorescence spectrum of an indocyanine green (ICG) fluorochrome.

Specifically, as illustrated in FIG. 19, in the case of the phosphor of example 2-1, since the fluorescence peak wavelength is 759 nm, the relative intensity of the excitation spectrum of ICG at this fluorescence peak wavelength is 80. The internal quantum efficiency of the phosphor of example 2-1 is 69%. Thus, the ICG absorption efficiency relative values of the phosphor of example 2-2 is 55.2. In the case of the phosphor of example 2-2, since the fluorescence peak wavelength is 760 nm, the relative intensity of the excitation spectrum of ICG at this fluorescence peak wavelength is 80. The internal quantum efficiency of the phosphor of example 2-2 is 78%. Thus, the ICG absorption efficiency relative values of the phosphor of example 2-2 is 62.4. The ICG absorption efficiency relative values of the phosphors of examples 2-3 and 2-4 are also calculated in the same manner, and the results are 64.6 and 54.9, respectively. The ICG absorption efficiency relative values of the phosphors of reference examples 2-1 and 2-2 are also calculated in the same manner, and the results are 48.0 and 39.1, respectively.

As illustrated in FIG. 18, the ICG absorption efficiency relative values of examples 2-1 to 2-4 were higher than those of reference examples 2-1 to 2-2. As a result, it is suggested that the phosphors of examples 2-1 to 2-4, that is, the phosphors represented by general formula (I), have high absorption efficiency of ICG and are preferable for a light emitting device utilizing the fluorescence imaging method.

Although the contents according to the present embodiment have been described above with reference to the examples, it is obvious to those skilled in the art that the present embodiment is not limited to these descriptions and that various modifications and improvements are possible.

The entire contents of Japanese Patent Application No. 2019-098537 (filing date: May 27, 2019) are incorporated herein by reference.

INDUSTRIAL APPLICABILITY

According to the present disclosure, there are provided a light emitting device capable of preventing the output saturation of fluorescence emitted by a phosphor even when a phosphor having a long luminescence lifetime is used, and an electronic device and an inspection method using the light emitting device.

REFERENCE SIGNS LIST 1, 1A, 1B, 1C Light emitting device
2 Light source
3, 3A Wavelength converter
4 First phosphor
6 Primary light
7 First wavelength-converted light
8 Second phosphor
9 Second wavelength-converted light

The invention claimed is:

1. A light emitting device, comprising:
a light source that emits a primary light having a light energy density exceeding 0.5 W/mm$^2$; and
a first phosphor that absorbs the primary light to convert the primary light into a first wavelength-converted light having a wavelength longer than that of the primary light,
wherein the first phosphor includes a compound serving as a host, the compound being a simple oxide including one kind of metal element or a composite oxide including a plurality of different kinds of the simple oxide as an end member,
when an energy conversion value at a peak wavelength of the primary light is E1 electron volts and an energy conversion value at a fluorescence peak wavelength of the first wavelength-converted light is E2 electron volts, a bandgap energy of a crystal of the simple oxide is larger than a sum of the E1 electron volts and the E2 electron volts, and the first wavelength-converted light includes fluorescence based on an electron energy transition of a transition metal ion, and the transition metal ion is Cr$^{3+}$.

2. The light emitting device according to claim 1, wherein the bandgap energy of the crystal of the simple oxide is 4.6 eV or more.

3. The light emitting device according to claim 1, wherein the first phosphor includes at least one element selected from the group consisting of Al, Ga, and Sc in a crystal of the compound serving as the host.

4. The light emitting device according to claim 1, wherein in the first phosphor, a cation element in a crystal of the compound serving as the host comprises only an element with a valence of three.

5. The light emitting device according to claim 1, wherein the primary light is a violet light having an emission peak in a wavelength range of 380 nm to less than 435 nm, or a blue light having an emission peak in a wavelength range of 435 nm to less than 470 nm.

6. The light emitting device according to claim 1, wherein the primary light is a laser beam.

7. The light emitting device according to claim 1, wherein the first wavelength-converted light is a near-infrared light having a fluorescence peak in a wavelength range of 700 nm to less than 1000 nm.

8. The light emitting device according to claim 1, wherein the first phosphor comprises two or more kinds of Cr$^{3+}$-activated phosphors.

9. The light emitting device according to claim 1, further comprising a second phosphor that absorbs the primary light and converts the primary light into a second wavelength-converted light that has a wavelength longer than that of the primary light and is different from the first wavelength-converted light.

10. The light emitting device according to claim 1, wherein the first phosphor is a phosphor having a composition formula represented by a following general formula (I):

$$(Gd_{1-x}La_x)_3(Ga_{1-y-z}Sc_yCr_z)_2Ga_3O_{12} \qquad (1)$$

where x, y, and z satisfy $0<x<1$, $0<y\leq0.60$, $0<z<0.2$.

11. The light emitting device according to claim 1, wherein the light emitting device is a medical light source or a medical lighting device.

12. The light emitting device according to claim 1, wherein the light emitting device is a medical light emitting device for use in a fluorescence imaging method or a photodynamic therapy.

13. The light emitting device according to claim 1, wherein the light emitting device is a light source for a sensing system or a lighting system for a sensing system.

14. An electronic device, comprising:
the light emitting device according to claim 1.

15. The electronic device according to claim 14, wherein the electronic device is any of an information recognition device, a sorting device, a detection device, or an inspection device.

16. The electronic device according to claim 15, wherein the inspection device is any of a medical inspection device, an agricultural and livestock inspection device, a fishery inspection device, or an industrial inspection device.

17. An inspection method, comprising:
using the light emitting device according to claim 1.

18. A light emitting device, comprising:
a light source that emits a primary light having a light energy density exceeding 0.5 $W/mm^2$; and
a first phosphor that absorbs the primary light to convert the primary light into a first wavelength-converted light having a wavelength longer than that of the primary light,
wherein the first phosphor includes a compound serving as a host, the compound being a simple oxide including one kind of metal element or a composite oxide including a plurality of different kinds of the simple oxide as an end member,
when an energy conversion value at a peak wavelength of the primary light is E1 electron volts and an energy conversion value at a fluorescence peak wavelength of the first wavelength-converted light is E2 electron volts, a bandgap energy of a crystal of the simple oxide is larger than a sum of the E1 electron volts and the E2 electron volts, and
the first wavelength-converted light includes fluorescence based on an electron energy transition of a transition metal ion, and an activator included in the first phosphor is at least one selected from the group consisting of $Cr^{3+}$, $V^{2+}$, $Mn^{4+}$, $Fe^{5+}$, $Ce^{3+}$, and $Eu^{2+}$.

* * * * *